US008815242B2

(12) United States Patent
Harvey

(10) Patent No.: US 8,815,242 B2
(45) Date of Patent: Aug. 26, 2014

(54) AVIAN DERIVED ANTIBODIES

(75) Inventor: Alex J. Harvey, Athens, GA (US)

(73) Assignee: Synageva BioPharma Corp., Lexington, MA (US)

( * ) Notice: Subject to any disclaimer, the term of this patent is extended or adjusted under 35 U.S.C. 154(b) by 365 days.

(21) Appl. No.: 12/800,989

(22) Filed: May 27, 2010

(65) Prior Publication Data

US 2010/0303806 A1 Dec. 2, 2010

Related U.S. Application Data

(60) Provisional application No. 61/217,138, filed on May 27, 2009.

(51) Int. Cl.
C07K 16/02 (2006.01)
C07K 16/28 (2006.01)
C07K 16/30 (2006.01)
A61K 39/395 (2006.01)
A01K 67/027 (2006.01)
C12N 15/85 (2006.01)

(52) U.S. Cl.
CPC ......... C12N 15/8509 (2013.01); A01K 2267/01 (2013.01); C07K 2317/41 (2013.01); A01K 2217/052 (2013.01); A01K 67/0275 (2013.01); C07K 16/2887 (2013.01); C07K 2317/732 (2013.01); A01K 2267/02 (2013.01); A01K 2227/30 (2013.01); C07K 2317/23 (2013.01); C07K 2317/734 (2013.01); C07K 2317/24 (2013.01); Y10S 424/80 (2013.01); Y10S 424/801 (2013.01); Y10S 530/867 (2013.01)
USPC .................. 424/144.1; 424/132.1; 424/133.1; 424/153.1; 424/155.1; 424/156.1; 424/173.1; 424/174.1; 424/800; 424/801; 530/387.3; 530/388.22; 530/388.73; 530/388.85; 530/867

(58) Field of Classification Search
None
See application file for complete search history.

(56) References Cited

U.S. PATENT DOCUMENTS

| 4,997,763 | A | 3/1991 | Hughes et al. |
| 5,011,780 | A | 4/1991 | Perry |
| 5,162,215 | A | 11/1992 | Bosselman et al. |
| 5,169,939 | A | 12/1992 | Gefter |
| 5,500,362 | A | 3/1996 | Robinson |
| 5,677,180 | A | 10/1997 | Robinson |
| 5,721,108 | A | 2/1998 | Robinson |
| 5,736,137 | A | 4/1998 | Anderson |
| 5,776,456 | A | 7/1998 | Anderson |
| 5,784,992 | A | 7/1998 | Petitte et al. |
| 5,834,251 | A | 11/1998 | Maras |
| 5,843,439 | A | 12/1998 | Anderson |
| 6,120,767 | A | 9/2000 | Robinson |
| 6,204,023 | B1 | 3/2001 | Robinson |
| 6,224,866 | B1 | 5/2001 | Barbera-Guillem |
| 6,331,415 | B1 | 12/2001 | Cabilly |
| 6,399,061 | B1 | 6/2002 | Anderson |
| 6,652,852 | B1 | 11/2003 | Robinson |
| 6,730,822 | B1 | 5/2004 | Ivarie et al. |
| 6,803,039 | B2 | 10/2004 | Tsuji |
| 6,803,225 | B2 | 10/2004 | Contreras |
| 6,825,396 | B2 | 11/2004 | MacArthur |
| 6,861,572 | B1 | 3/2005 | Etches et al. |
| 6,893,625 | B1 | 5/2005 | Robinson |
| 6,897,044 | B1 | 5/2005 | Braslawsky et al. |
| 6,946,292 | B2 | 9/2005 | Kanda |
| 6,991,790 | B1 | 1/2006 | Lam |
| 7,029,872 | B2 | 4/2006 | Gerngross |
| 7,064,191 | B2 | 6/2006 | Skinkawa |
| 7,129,390 | B2 | 10/2006 | Ivarie et al. |
| 7,151,164 | B2 | 12/2006 | Hansen |
| 7,214,775 | B2 | 5/2007 | Hanai |
| 7,252,933 | B2 | 8/2007 | Contreras |
| 7,326,681 | B2 | 2/2008 | Gerngross |
| 7,332,299 | B2 | 2/2008 | Hamilton |
| 7,335,761 | B2 | 2/2008 | Harvey |
| 7,381,560 | B2 | 6/2008 | Anderson |
| 7,422,739 | B2 | 9/2008 | Anderson |
| 7,511,120 | B2 | 3/2009 | Ivarie et al. |
| 2002/0155998 | A1 | 10/2002 | Young et al. |
| 2002/0197255 | A1 | 12/2002 | Anderson |
| 2003/0126629 | A1 | 7/2003 | Rapp et al. |
| 2003/0147885 | A1 | 8/2003 | Anderson |
| 2003/0170888 | A1 | 9/2003 | Van de Lavoir et al. |
| 2003/0172387 | A1 | 9/2003 | Zhu et al. |
| 2004/0018590 | A1 | 1/2004 | Gerngross |
| 2004/0019922 | A1 | 1/2004 | Ivarie et al. |

(Continued)

FOREIGN PATENT DOCUMENTS

EP 0274394 A3 1/1990
EP 0669836 B1 7/1996

(Continued)

OTHER PUBLICATIONS

Reff, B.E. et al. "Depletion of B cells in vivo by a chimeric mouse human monoclonal antibody to CD20", Blood, Jan. 15, 1994, vol. 83, No. 2, pp. 435-445.
Kamihira, M. et al. "Production of chimeric monoclonal antibodies by genetically manipulated chickens", Journal of Biotechnology, Mar. 17, 2009, vol. 141, pp. 18-25.
Houdebine, L. M. "Production of pharmaceutical proteins by transgenic animals", Comparative Immunology Microbiology and Infectious Diseases, Feb. 19, 2009, vol. 32, pp. 107-121.
Allioli et al. "Use of retroviral vectors to introduce and express the β-galactosidase marker gene in cultured chicken primordial germ cells," Developmental Biology, 1994, 165:30-37.

(Continued)

Primary Examiner — Ronald Schwadron
(74) Attorney, Agent, or Firm — Hak J. Chang

(57) ABSTRACT

The invention is drawn to a composition comprising an isolated mixture of cytotoxic anti-CD20 antibody molecules produced in a transgenic avian. The antibody molecules have a heavy chain and a light chain whose amino acid sequences set forth in SEQ ID NOs: 4 and 5 and exhibit an increased level of cytotoxicity as compared to anti-CD20 antibody molecules produced in CHO cells.

6 Claims, 10 Drawing Sheets

(56) References Cited

U.S. PATENT DOCUMENTS

| | | |
|---|---|---|
| 2004/0019923 A1 | 1/2004 | Ivarie et al. |
| 2004/0072290 A1 | 4/2004 | Umana |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0136986 A1 | 7/2004 | Raju |
| 2004/0191256 A1 | 9/2004 | Raju |
| 2004/0230042 A1 | 11/2004 | Hamilton |
| 2005/0074843 A1 | 4/2005 | Umana |
| 2005/0114916 A1 | 5/2005 | Etches et al. |
| 2005/0163708 A1 | 7/2005 | Robinson |
| 2005/0227315 A1 | 10/2005 | Pain |
| 2005/0262593 A1 | 11/2005 | Kanda |
| 2005/0271658 A1 | 12/2005 | Brunetta |
| 2005/0272128 A1 | 12/2005 | Umana |
| 2005/0272916 A1 | 12/2005 | Hanai |
| 2006/0002930 A1 | 1/2006 | Brunetta |
| 2006/0021071 A1 | 1/2006 | Satoh |
| 2006/0024292 A1 | 2/2006 | Gerngross |
| 2006/0024295 A1 | 2/2006 | Brunetta |
| 2006/0024300 A1 | 2/2006 | Adams |
| 2006/0024304 A1 | 2/2006 | Gerngross |
| 2006/0024800 A1 | 2/2006 | Hanai |
| 2006/0034828 A1 | 2/2006 | Gerngross |
| 2006/0034829 A1 | 2/2006 | Gerngross |
| 2006/0034830 A1 | 2/2006 | Gerngross |
| 2006/0034835 A1 | 2/2006 | Adams |
| 2006/0063254 A1 | 3/2006 | Kanda |
| 2006/0064781 A1 | 3/2006 | Kanda |
| 2006/0078990 A1 | 4/2006 | Kanda |
| 2006/0078991 A1 | 4/2006 | Kanda |
| 2006/0148035 A1 | 7/2006 | Gerngross |
| 2006/0171921 A1 | 8/2006 | Ivarie et al. |
| 2006/0177898 A1 | 8/2006 | Gerngross |
| 2006/0188495 A1 | 8/2006 | Barron |
| 2006/0191026 A1 | 8/2006 | Zhu et al. |
| 2006/0223147 A1 | 10/2006 | Nishiya |
| 2006/0257399 A1 | 11/2006 | Gerngross |
| 2006/0286637 A1 | 12/2006 | Hamilton |
| 2007/0010009 A1 | 1/2007 | Kanda |
| 2007/0020259 A1 | 1/2007 | Hansen |
| 2007/0020260 A1 | 1/2007 | Presta |
| 2007/0037248 A1 | 2/2007 | Bobrowicz |
| 2007/0071745 A1 | 3/2007 | Umana |
| 2007/0077650 A1 | 4/2007 | Harvey |
| 2007/0092486 A1 | 4/2007 | Yesland |
| 2007/0105127 A1 | 5/2007 | Gerngross |
| 2007/0111281 A1 | 5/2007 | Sondermann |
| 2007/0128691 A1 | 6/2007 | Nakano |
| 2007/0166300 A1 | 7/2007 | Hanai |
| 2007/0166301 A1 | 7/2007 | Hanai |
| 2007/0166302 A1 | 7/2007 | Hanai |
| 2007/0166303 A1 | 7/2007 | Hanai |
| 2007/0166304 A1 | 7/2007 | Hanai |
| 2007/0166305 A1 | 7/2007 | Hanai |
| 2007/0178551 A1 | 8/2007 | Gerngross |
| 2007/0207151 A1 | 9/2007 | Hanai |
| 2007/0243165 A1* | 10/2007 | Ivarie et al. .......... 424/85.7 |
| 2008/0064862 A1 | 3/2008 | Harvey |
| 2009/0074718 A1 | 3/2009 | Ivarie et al. |
| 2009/0083871 A1 | 3/2009 | Etches et al. |
| 2009/0083872 A1 | 3/2009 | Etches et al. |

FOREIGN PATENT DOCUMENTS

| | | |
|---|---|---|
| EP | 1865058 A1 | 12/2007 |
| WO | WO 94/20608 | 9/1994 |
| WO | WO 97/33998 | 9/1997 |
| WO | WO 02060955 A2 * | 8/2002 |
| WO | WO 03/081993 | 10/2003 |
| WO | WO 2004/015123 | 2/2004 |
| WO | WO 2004/047531 | 6/2004 |
| WO | 2005-040215 A2 | 5/2005 |
| WO | 2006-084035 A2 | 8/2006 |
| WO | WO 2006/126069 | 2/2008 |
| WO | WO 2008/017704 | 2/2008 |

OTHER PUBLICATIONS

Anderson et al. "Monosaccharide and oligosaccharide analysis of isoelectric focusing-separated and blotted granulocyte colony-stimulating factor glycoforms using high-pH . . . ," Glycobiology, 1994, 4(4):459-467.

Archer et al. "Human growth hormone (hgh) secretion in milk of goats after direct transfer of the hgh gene into the emammary gland by using . . . ," Proc. Natl. Acad. Sci. USA, 1994, 91:6840-6844.

Bosselman et al. "Germline transmission of exogenous genes in the chicken," Science, 1989, 243:533-535.

Bosselman et al. "Replication-Defective Vectors of Reticuloendotheliosis Virus Transduce Exogenous Genes into Somatic Stem Cells of the Unincubated Chicken Embryo," J Virol, 1989, 63(6):2680-2689.

Carter et al. The significance of carbohydrates on G-CSF: differential sensitivity of G-CSFs to human neutrophil elastase degradation, journal of leukocyte Biology, 2004, 75: 515-522.

Cosset et al. "Improvement of avian leucosis virus (ALV)-based retrovirus vectors by suing different cisacting sequences from ALVs," Journal of Virology, 1991, 65:3388-3394.

Cosset et al. "Use of helper cells with two host ranges to generate high-titer retroviral vectors," Virology, 1993, 193:385-395.

Dierich et al, "Cell-specificity of the chicken ovalbumin and conalbumin promoters," The EMBO Journal, 1987, 6:2305-2312.

Du et al. "Crystal structure of chimeric antibody C2H7 Fab in complex with a CD20 peptide," Molecular Immunology, 2008, 45, 2861-2868.

Etches et al. "Chimeric Chickens and Their Use in Manipulation of the Chicken Genome," Poultry Science, 1993, 72:882-889.

Etches et al. "Manipulation of Blastodermal Cells," Poultry Science, 1997, 76:1075-1083.

Etches et al. "Contributions to Somatic and Germline Lineages of Chicken Blastodermal Cells Maintained in Culture," Mol Repro Dev, 1996, 45:291-298.

Etches et al. "Strategies for the production of transgenic chicken." Methods Mol Biol, 1997, 22:433-450.

Etches. "Response to Ivarie: Competitive bioreactor hens on the horizon," Trends in Biotechnology, 2006, 24(3):101-102.

Etches et al. "The hard cell(s) of avian transgenesis," Transgenic Res, 2006, 15:521-526.

Gillies et al. "An anti-CD20-IL02 immunocytokine is highly efficacious in a SCID mouse model of established human B lymphoma," Blood, 2005, 105:3972-3978.

Harvey et al. "Consistent Production of Transgenic Chickens Using Replication-Deficient Retroviral Vectors and High-Throughput Screening procedures," Poultry Science, 2002, 81:202-212.

Harvey et al. "Expression of exogenous protein in the egg white of transgenic chickens," Nature Biotechnology, 2002, 19:396-399.

Harvey et al. "Validating the Hen as a Bioreactor for the Production of Exogenous proteins in Egg White," Poultry Science, 2003, 82:927-930.

Idusogie et al. "Mapping of the C1q Binding Site on Rituxan, a Chimeric Antibody with a Human IgG1 Fc," The Journal of Immunology, 2000, 164:4178-4184.

Ivarie et al. Avian Transgenesis: Progress Towards the Promise, Trends in Biotechnology, 2003, 21(1).

Lee et al. "Generation and characterization of a novel single-gene-encoded single-chain immunoglobulin molecule with antigen binding activity and effector functions," Molecular Immunology, 1999, 36:61-71.

Li et al. "Optimization of humanized IgGs in glycoengineered *Pichia pastoris*," Nature Biotechnology, 2006, 24(2):210-215.

Love et al. "Transgenic birds by DNA microinjection," Bio/Technology, 1994, 12:60-63.

Salter et al. "Gene Insertion into the Chicken Germ Line by Retroviruses," Poultry Science, 1986, 65:1445-1458.

(56) References Cited

OTHER PUBLICATIONS

Salter et al. "Transgenic Chickens: Insertion of Retroviral Genes into the Chicken Germ Line," Virology, 1987, 157:236-240.

Takeuchi et al. Role of Sugar Chains in the in Vitro Biological Activity of Human Erythropoietin Produced in Recombinant Chinese Hamster Ovary Cells*, The Journal of Biological Chemistry, 1990, 265(21):12127-12130.

Tang et al. "High level expression of a functional human/mouse chimeric anti-CD20 monoclonal antibody in milk of transgenic mice," Transgenic Res, 2008, 17:727-732.

Van De Lavoir et al. "Germline transmission of genetically modified primordial germ cells," Nature, 2006, 441:766-769.

Watanabe et al. "Distribution analysis of transferred donor cells in avian blastodermal chimeras," Development, 1992, 114:331-338.

Zhu et al. "Production of human monoclonal antibody in eggs of chimeric chickens," Nature Biotechnology, 2005, 23:1159-1169.

Anderson and Sando. "Cloning and Expression of cDNA Encoding Human Lysosomal Acid Lipase/Cholesteryl Este Hydrolase," Journal of Biological Chemistry, 1991, 266(33):22479-22484.

Sorge et al. "Molecular cloning and nucleotide sequence of human glucocerebrosidase cDNA," Proc. Natl. Acad. Sci., 1985, 82:7289-7293.

Tsuji et al. "Nucleotide Sequence of cDNA containing the complete coding sequence for Human Lysosomal Glucocerebrosidase", The Journal of Biological Chemistry, 1986, 261(1):50-53.

\* cited by examiner

LC
*mdfqviisfllisasvimsrg*qivlsqspailsaspgekvtmt
crasssvsyihwfqqkpgsspkpwiyatsnlasgvpvrfsgsgs
gtsysltisrveaedaatyycqqwtsnpptfgggtkleikrtva
apsvfifppsdeqlksgtasvvcllnnfypreakvqwkvdnalq
sgnsqesvteqdskdstyslsstltlskadyekhkvyacevthq
glsspvtksfnrgec*

HC
*mgwslillflvavatrvls*qvqlqqpgaelvkpgasvkmsckas
gytftsynmhwvkqtpgrglewigaiypgngdtsynqkfkgkat
ltadkssstaymqlssltsedsavyycarstyyggdwyfnvwga
gttvtvsaastkgpsvfplapsskstsggtaalgclvkdyfpep
vtvswnsgaltsgvhtfpavlqssglyslssvvtvpssslgtqt
yicnvnhkpsntkvdkkaepkscdkthtcppcpapellggpsvf
lfppkpkdtlmisrtpevtcvvvdvshedpevkfnwyvdgvevh
naktkpreeqynstyrvvsvltvlhqdwlngkeykckvsnkalp
apiektiskakgqprepqvytlppsrdeltknqvsltclvkgfy
psdiavewesngqpennykttppvldsdgsfflyskltvdksrw
qqgnvfscsvmhealhnhytqkslslspgk*

Figure 3

Single Chain Anti CD-20
mdfqvqiisfllisasvimsrgqivlsqspailsaspgekvtmt
crasssvsyihwfqqkpgsspkpwiyatsnlasgvpvrfsgsgs
gtsysltisrveaedaatyycqqwtsnpptfgggtkleikrtva
apsvfifppsdeqlksgtasvvcllnnfypreakvqwkvdnalq
sgnsqesvteqdskdstyslsstltlskadyekhkvyacevthq
glsspvtksfnrgecggggsggggsggggsggggsggggsgggg
sqvqlqqpgaelvkpgasvkmsckasgytftsynmhwvkqtpgr
glewigaiypgngdtsynqkfkgkatltadkssstaymqlsslt
sedsavyycarstyyggdwyfnvwgagttvtvsaastkgpsvfp
lapssksts ggtaalgclvkdyfpepvtvswnsgaltsgvhtfp
avlqssglyslssvvtvpssslgtqtyicnvnhkpsntkvdkka
epkscdkthtcppcpapellggpsvflfppkpkdtlmisrtpev
tcvvvdvshedpevkfnwyvdgvevhnaktkpreeqynstyrvv
svltvlhqdwlngkeykckvsnkalpapiektiskakgqprepq
vytlppsrdeltknqvsltclvkgfypsdiavewesngqpenny
kttppvldsdgsfflyskltvdksrwqqgnvfscsvmhealhnh
ytqkslslspgk*

Figure 4

C2H7 anti-CD20 HC
Qaylqqsgaelvrpgasvkmsckasgytftsynmhwvkqtprqg
lewigaiypgngdtsynqkfkgkatltvdkssstaymqlsslts
edsavyfcarvvyysnsywyfdvwgtgttvtvsaastkgpsvfp
lapsskstsggtaalgclvkdyfpepvtvswnsgaltsgvhtfp
avlqssglyslssvvtvpssslgtqtyicnvnhkpsntkvdkkv
epkscd

C2H7 anti-CD20 LC
qivlsqspailsaspgekvtmtcrasssvsymhwyqqkpgsspk
pwiyapsnlasgvparfsgsgsgtsysltisrveaedaatyycq
qwsfnpptfgagtklelkrtvaapsvfifppsdeqlksgtasvv
cllnnfypreakvqwkvdnalqsgnsqesvteqdskdstyslss
tltlskadyekhkvyacevthqglsspvtksfnrgec

SEQUENCE LISTING

```
<160> NUMBER OF SEQ ID NOS: 9

<210> SEQ ID NO 1
<211> LENGTH: 235
<212> TYPE: PRT
<213> ORGANISM: Artificial
<220> FEATURE:
<223> OTHER INFORMATION: LC

<400> SEQUENCE: 1

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
```

```
                115                 120                 125
Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
            210                 215                 220

Pro Val Thr Lys Ser Phe Asn Arg Gly Glu Cys
225                 230                 235

<210> SEQ ID NO 2
<211> LENGTH: 470
<212> TYPE: PRT
<213> ORGANISM: Artificial
<220> FEATURE:
<223> OTHER INFORMATION: HC

<400> SEQUENCE: 2

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
                20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
        50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ala Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
```

```
            245                 250                 255
Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 3
<211> LENGTH: 716
<212> TYPE: PRT
<213> ORGANISM: Artificial
<220> FEATURE:
<223> OTHER INFORMATION: Single Chain Anti CD-20

<400> SEQUENCE: 3

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
            35                  40                  45

Ser Ser Val Ser Tyr Ile His Trp Phe Gln Gln Lys Pro Gly Ser Ser
        50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
            115                 120                 125

Arg Thr Val Ala Ala Pro Ser Val Phe Ile Phe Pro Pro Ser Asp Glu
```

```
                130                 135                 140
Gln Leu Lys Ser Gly Thr Ala Ser Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
                210                 215                 220

Pro Val Thr Lys Ser Phe Asn Arg Gly Glu Cys Gly Gly Gly Gly Ser
225                 230                 235                 240

Gly Gly Gly Gly Ser Gly Gly Gly Ser Gly Gly Gly Gly Ser Gly
                245                 250                 255

Gly Gly Gly Ser Gly Gly Gly Ser Gln Val Gln Leu Gln Gln Pro
                260                 265                 270

Gly Ala Glu Leu Val Lys Pro Gly Ala Ser Val Lys Met Ser Cys Lys
                275                 280                 285

Ala Ser Gly Tyr Thr Phe Thr Ser Tyr Asn Met His Trp Val Lys Gln
290                 295                 300

Thr Pro Gly Arg Gly Leu Glu Trp Ile Gly Ala Ile Tyr Pro Gly Asn
305                 310                 315                 320

Gly Asp Thr Ser Tyr Asn Gln Lys Phe Lys Gly Lys Ala Thr Leu Thr
                325                 330                 335

Ala Asp Lys Ser Ser Ser Thr Ala Tyr Met Gln Leu Ser Ser Leu Thr
                340                 345                 350

Ser Glu Asp Ser Ala Val Tyr Tyr Cys Ala Arg Ser Thr Tyr Tyr Gly
                355                 360                 365

Gly Asp Trp Tyr Phe Asn Val Trp Gly Ala Gly Thr Thr Val Thr Val
                370                 375                 380

Ser Ala Ala Ser Thr Lys Gly Pro Ser Val Phe Pro Leu Ala Pro Ser
385                 390                 395                 400

Ser Lys Ser Thr Ser Gly Gly Thr Ala Ala Leu Gly Cys Leu Val Lys
                405                 410                 415

Asp Tyr Phe Pro Glu Pro Val Thr Val Ser Trp Asn Ser Gly Ala Leu
                420                 425                 430

Thr Ser Gly Val His Thr Phe Pro Ala Val Leu Gln Ser Ser Gly Leu
                435                 440                 445

Tyr Ser Leu Ser Ser Val Val Thr Val Pro Ser Ser Ser Leu Gly Thr
                450                 455                 460

Gln Thr Tyr Ile Cys Asn Val Asn His Lys Pro Ser Asn Thr Lys Val
465                 470                 475                 480

Asp Lys Lys Ala Glu Pro Lys Ser Cys Asp Lys Thr His Thr Cys Pro
                485                 490                 495

Pro Cys Pro Ala Pro Glu Leu Leu Gly Gly Pro Ser Val Phe Leu Phe
                500                 505                 510

Pro Pro Lys Pro Lys Asp Thr Leu Met Ile Ser Arg Thr Pro Glu Val
                515                 520                 525

Thr Cys Val Val Val Asp Val Ser His Glu Asp Pro Glu Val Lys Phe
                530                 535                 540

Asn Trp Tyr Val Asp Gly Val Glu Val His Asn Ala Lys Thr Lys Pro
545                 550                 555                 560
```

Arg Glu Glu Gln Tyr Asn Ser Thr Tyr Arg Val Val Ser Val Leu Thr
                565                 570                 575

Val Leu His Gln Asp Trp Leu Asn Gly Lys Glu Tyr Lys Cys Lys Val
            580                 585                 590

Ser Asn Lys Ala Leu Pro Ala Pro Ile Glu Lys Thr Ile Ser Lys Ala
        595                 600                 605

Lys Gly Gln Pro Arg Glu Pro Gln Val Tyr Thr Leu Pro Pro Ser Arg
    610                 615                 620

Asp Glu Leu Thr Lys Asn Gln Val Ser Leu Thr Cys Leu Val Lys Gly
625                 630                 635                 640

Phe Tyr Pro Ser Asp Ile Ala Val Glu Trp Glu Ser Asn Gly Gln Pro
                645                 650                 655

Glu Asn Asn Tyr Lys Thr Thr Pro Pro Val Leu Asp Ser Asp Gly Ser
            660                 665                 670

Phe Phe Leu Tyr Ser Lys Leu Thr Val Asp Lys Ser Arg Trp Gln Gln
        675                 680                 685

Gly Asn Val Phe Ser Cys Ser Val Met His Glu Ala Leu His Asn His
    690                 695                 700

Tyr Thr Gln Lys Ser Leu Ser Leu Ser Pro Gly Lys
705                 710                 715

<210> SEQ ID NO 4
<211> LENGTH: 226
<212> TYPE: PRT
<213> ORGANISM: Artificial
<220> FEATURE:
<223> OTHER INFORMATION: C2H7 Anti-CD20 HC

<400> SEQUENCE: 4

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Ala Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

```
His Lys Pro Ser Asn Thr Lys Val Asp Lys Lys Val Glu Pro Lys Ser
    210                 215                 220

Cys Asp
225

<210> SEQ ID NO 5
<211> LENGTH: 213
<212> TYPE: PRT
<213> ORGANISM: Artificial
<220> FEATURE:
<223> OTHER INFORMATION: C2H7 Anti-CD20 LC

<400> SEQUENCE: 5

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 6
<211> LENGTH: 10762
<212> TYPE: DNA
<213> ORGANISM: Artificial
<220> FEATURE:
<223> OTHER INFORMATION: pSIN-OV-1.1-I-SBC201-I3

<400> SEQUENCE: 6
cttctgggca tccttcagcc ccttgttgaa tacgcttgag gagagccatt tgactctttc       60
cacaactatc caactcacaa cgtggcactg gggttgtgcc gcctttgcag gtgtatctta     120
tacacgtggc ttttggccgc agaggcacct gtcgccaggt gggggggttcc gctgcctgca    180 aagggtcgct acagacgttg tttgtcttca agaagcttcc agaggaactg cttccttcac     240
gacattcaac agaccttgca ttcctttggc gagaggggaa agaccctag gaatgctcgt      300
```

```
caagaagaca gggccaggtt tccgggccct cacattgcca aaagacggca atatggtgga      360
aaataacata tagacaaacg cacaccggcc ttattccaag cggcttcggc cagtaacgtt      420 agggggggg gagggagagg ggcggaattc caccacactg gactagtgga tcctcaacac      480
tctcccctgt tgaagctctt tgtgacgggc gagctcaggc cctgatgggt gacttcgcag      540
gcgtagactt tgtgtttctc gtagtctgct ttgctcagag tcagggtgct gctgaggctg      600
taggtgctgt ccttgctgtc ctgctctgtg acactctcct gggagtttcc cgattggagg      660
gcgttatcaa ccttccactg tactttggcc tctctgggat agaagttatt cagcaggcac      720
acaacagagg cagttccaga tttcaactgc tcatcagatg gcgggaagat gaagacagat      780
ggtgcagcca ccgtacgttt gatttccagc ttggtccccc ctccgaacgt gggtgggtta      840
ctagtccact gctggcagta ataagtggca gcatcttcag cctccactct gctgattgtg      900
agagagtaag aagtcccaga cccactgcca ctgaagcgaa cagggactcc agaagccagg      960
ttggatgtgg cataaatcca aggttttggg gaggatcctg gcttttgctg gaaccagtgg     1020
atgtaactga cacttgagct ggccctgcaa gtcattgtga ccttctcccc gggagatgca     1080
gacaggattg ccggagattg ggagagaaca atttgtcctc tggacattat gactgaagca     1140
ctgattagca ggaagctgat aatctgcacc tgaaaatcca tggtgaactc tgagttgtct     1200
agagcaaaca gcagaacagt gaaaatgtaa ggatggaatg ctgtacatag taccatgcag     1260
ggtactctat ggtaggctac aacagtaaat tacgagcagt ttttaggcaa ttaaatgtta     1320
acaagtagtt ttaaagtaat tctgtggtaa tgtgtctgtt gctatatcca cctctcatgt     1380
gcatgttcaa aaccatattc ataaatctat ttatgtattt gcattcagtt gtcttttggg     1440
tagcaaactg tcccagaagc cagttgcctc tacatatttt tgttcagtga aagctagaat     1500
tcattgatac ttttcagtac ctctgattaa aacacaatct gataggcttg caaaactgga     1560
aattcaaaga gcaaatttca gtaaacttta ggtttggaca gatatatgag aaagcagagg     1620
cttgctgact attttatttc ttatttttat tccctaaaaa taaatgtaga gaaatatctg     1680
tttgttgcac actacttgct atgagtagat cttcaaaagt attttttacct ttgttttggt     1740 gatggcagaa tagataagga atgtaattta tatggggtca tgtagtctag gagaaagaca     1800
cgcatgtaat tcatattctg ctctattgca cttttcaggta tggtttgctt tgctcaaaga     1860
tatgcatgtg tactgtagta taaactttct gtggagttaa attttagtgg tgacattcag     1920
acagaagaga aatgcagaca tgataaaata gcaatgttta ctataaaaca gagccactga     1980
atgaattctt gttcatgaca tagaccaata gaagatttat acttgttctg tctgtttcta     2040
ttataaagag ctgaactgta caactattgt atagccagtg tgcttatata aagcacagct     2100
tttggagcca gcatgaatct agttgctttc ctgagattta tataatctgt gaaagtcaga     2160
agtccttcag agcccagccc tttatatgcg tactgagtgc tggggcctca ggattggatt     2220
ttctgtatta aacccctcaa agttttttac tgaccacgtg tgtgagtata cacacacaca     2280
tttttctcat tttcttttct gtatataagt tcacatgtat ctattattgt aagaatatac     2340
gtttatgcac cccccacatt tttatcttgt gtagtgatca gcagctgcac tttgcaggaa     2400
ttaaacttct agagaatttt cacattaaaa taactcccca gaattcactg aacaccatga     2460
ttttgctctc tgtgcactct gtagggctag aagttaatca agcaaactgc aaagcatatc     2520
agatagtgaa cgacaggata agatgttctg aaattaaaaa catattttaa gcacaaagaa     2580
taagcctcct gaaaacaaac acaaagcttt tacacataat aaaatagtgc agaatgcata     2640
cacaggtgag aagttttat aggggtatc acgcaggtac ttcacccctta aagatacaac     2700
```

```
acatagcaca ataattgtta atttttaaa gtttaggtgc aagtaagagc taatatagag    2760
agaaggtaat tccagagagt tgcttacctt tcgagcttga ctgctaaagg caatacagct    2820
ttctagctgt atgtacagac actggctgag ccctggggaa tatatagtct gaattgtgac    2880
ccacccacag gttcccttca gaagtttgac ctttgacacc atagaaatca tttaatggga    2940 ttggttaga ttttagtttc aataggtcca ttttggattg aatggagagc aaatattagt     3000
ttttaattct gggtaacaat gtgttttctg cctgttctgc taatccatca ggactgttgg    3060
atgggagaga agactgggaa atattgctca tgttccattg agcttcagtt acaaccagat    3120
aatgggatct ttaagaaaac agaaaaatgt gggaaccttg gagatggaaa acataattag    3180
caattattag ttagtgtgct tattactatg gttgtagtaa cagaccagaa gtctgtttca    3240
tttgatcctt cttgtatgta caatgtgcat ctgagccacg ctagacagga cataaatgag    3300
aacaagactt gacctattat tttcttgaca aaataggaga aataagaag cgtgcatgtg     3360 aaggagccaa ctgagactag agtgaagagc agacacactt tctttcctat agttggaata    3420
tttaaatcta tcttttatg ggtgtgaatg ctttataaca aacttttatt ctgaggatac     3480
agcaaaacat agctccatac aatgcaaaac aatactcaat ttcaaatgtg tttatgatat    3540
gaacttgcag tgttcctcaa agatcttcca tgaataactt aatggcctgg cagatgacag    3600
aggaattgtg aaattcagct ggaggagtgt tcatggttcg agggacaatc ataatataca    3660
atagcaaata tatttcagtt atagaagcta ttgttctgta ttgaaataat agaattgaca    3720
aacagtaaag aaaccattct gacctctgta aagcactgtt tgatttaaaa atgggggaaa    3780
aaagtacaac ataattcttc aggacataca tagagatcac tgcaatctct gttaagcaga    3840 attacttttcc tataccacta gctgaagttt agtcagtgcc attttctttt gtttctctcc    3900
ttccttttgt gaaaacatat atactgtgga aatctacatt ctccttgcca agtctgagga    3960
cttaacgagg aatataaaaa aattacagga ggcttataag cagcccgaaa gaagagcgta    4020
ggcgagttct tgtattccgt gtgatagctg gttggattgg taattgatcg gctggcacgc    4080
ggaatatagg aggtcgctga atagtaaact tgtagacttg gctacagcat agagtatctt    4140
ctgtagctct gatgactgct aggaaataat gctacggata atgtggggag ggcaaggctt    4200
gcgaatcggg ttgtaacggg caaggcttga ctgagggac aatagcatgt ttaggcgaaa     4260 agcgggctt cggttgtacg cggttaggag tcccctcagg atatagtagt ttcgcttttg     4320
catagggagg gggacggatt ggacgaacca ctgaattccg cattgcagag atattgtatt    4380
taagtgccta gctcgataca ataaacgcca tttgaccatt caccacattg gtgtgcacct    4440
gggttgatgg ccggaccgtt gattccctga cgactacgag cacatgcatg aagcagaagg    4500
cttcatttgg tgaccccgac gtgatcgtta gggaatacgc gctcactggc cgtcgtttta    4560
caacgtcgtg actgggaaaa ccctggcgtt acccaactta atcgccttgc agcacatccc    4620
cctttcgcca gctggcgtaa tagcgaagag gcccgcaccg atcgcccttc caacagttg     4680 cgcagcctga atggcgaatg gaaattgtaa gcgttaatat tttgttaaaa ttcgcgttaa    4740 attttttgtta aatcagctca ttttttaacc aataggccga atcggcaaa atcccttata    4800 aatcaaaaga atagaccgag atagggttga gtgttgttcc agtttggaac aagagtccac    4860
tattaaagaa cgtggactcc aacgtcaaag ggcgaaaaac cgtctatcag ggcgatggcc    4920
cactacgtga accatcaccc taatcaagtt ttttggggtc gaggtgccgt aaagcactaa    4980
atcggaaccc taagggagc ccccgattta gagcttgacg gggaaagccg gcgaacgtgg     5040
```

-continued

```
cgagaaagga agggaagaaa gcgaaaggag cgggcgctag ggcgctggca agtgtagcgg     5100
tcacgctgcg cgtaaccacc acacccgccg cgcttaatgc gccgctacag ggcgcgtcag     5160
gtggcacttt tcggggaaat gtgcgcggaa cccctatttg tttattttc taaatacatt      5220
caaatatgta tccgctcatg agacaataac cctgataaat gcttcaataa tattgaaaaa     5280
ggaagagtat gagtattcaa catttccgtg tcgcccttat tcccttttt gcggcatttt      5340
gccttcctgt ttttgctcac ccagaaacgc tggtgaaagt aaaagatgct gaagatcagt     5400
tgggtgcacg agtgggttac atcgaactgg atctcaacag cggtaagatc cttgagagtt     5460
ttcgccccga agaacgtttt ccaatgatga gcacttttaa agttctgcta tgtggcgcgg     5520
tattatcccg tattgacgcc gggcaagagc aactcggtcg ccgcatacac tattctcaga     5580
atgacttggt tgagtactca ccagtcacag aaaagcatct tacgatggc atgcagtaa       5640
gagaattatg cagtgctgcc ataaccatga gtgataacac tgcggccaac ttacttctga     5700
caacgatcgg aggaccgaag gagctaaccg cttttttgca caacatgggg gatcatgtaa     5760
ctcgccttga tcgttgggaa ccggagctga atgaagccat accaaacgac gagcgtgaca     5820
ccacgatgcc tgtagcaatg gcaacaacgt tgcgcaaact attaactggc gaactactta     5880
ctctagcttc ccggcaacaa ttaatagact ggatggaggc ggataaagtt gcaggaccac     5940
ttctgcgctc ggcccttccg gctggctggt ttattgctga taaatctgga gccggtgagc     6000
gtgggtctcg cggtatcatt gcagcactgg ggccagatgg taagccctcc cgtatcgtag     6060
ttatctacac gacggggagt caggcaacta tggatgaacg aaatagacag atcgctgaga     6120
taggtgcctc actgattaag cattggtaac tgtcagacca agtttactca tatatacttt     6180
agattgattt aaaacttcat ttttaattta aaaggatcta ggtgaagatc ctttttgata     6240
atctcatgac caaaatccct taacgtgagt tttcgttcca ctgagcgtca gaccccgtag     6300
aaaagatcaa aggatcttct tgagatcctt ttttctgcg cgtaatctgc tgcttgcaaa      6360
caaaaaaacc accgctacca gcggtggttt gtttgccgga tcaagagcta ccaactcttt     6420
ttccgaaggt aactggcttc agcagagcgc agataccaaa tactgtcctt ctagtgtagc     6480
cgtagttagg ccaccacttc aagaactctg tagcaccgcc tacatacctc gctctgctaa     6540
tcctgttacc agtggctgct gccagtggcg ataagtcgtg tcttaccggg ttggactcaa     6600
gacgatagtt accggataag gcgcagcggt cgggctgaac ggggggttcg tgcacacagc     6660
ccagcttgga gcgaacgacc tacaccgaac tgagatacct acagcgtgag ctatgagaaa     6720
gcgccacgct tcccgaaggg agaaaggcgg acaggtatcc ggtaagcggc agggtcggaa     6780
caggagagcg cacgagggag cttccagggg gaaacgcctg gtatctttat agtcctgtcg     6840
ggtttcgcca cctctgactt gagcgtcgat ttttgtgatg ctcgtcaggg gggcggagcc     6900
tatggaaaaa cgccagcaac gcggcctttt tacggttcct ggccttttgc tggccttttg     6960
ctcacatgtt ctttcctgcg ttatcccctg attctgtgga taaccgtatt accgcctttg     7020
agtgagctga taccgctcgc cgcagccgaa cgaccgagcg cagcgagtca gtgagcgagg     7080
aagcggaaga gcgcccaata cgcaaaccgc ctctccccgc gcgttggccg attcattaat     7140
gcagctggca cgacaggttt cccgactgga aagcgggcag tgagcgcaac gcaattaatg     7200
tgagttagct cactcattag gcaccccagg ctttacactt tatgcttccg gctcgtatgt     7260
tgtgtggaat tgtgagcgga taacaatttc acacaggaaa cagctatgac catgattacg     7320
ccaagcgcgc attggtaatt gatcggctgg cacgcggaat ataggaggtc gctgaatagt     7380
aaacttgtag acttggctac agcatagagt atcttctgta gctctgatga ctgctaggaa     7440
```

```
ataatgctac ggataatgtg gggagggcaa ggcttgcgaa tcgggttgta acgggcaagg    7500
cttgactgag gggacaatag catgtttagg cgaaaagcgg ggcttcggtt gtacgcggtt    7560
aggagtcccc tcaggatata gtagtttcgc ttttgcatag ggaggggaa atgtagtctt     7620 atgcaatact cttgtagtct tgcaacatgc ttatgtaacg atgagttagc aacatgcctt    7680
ataaggagag aaaaagcacc gtgcatgccg attggtggga gtaaggtggt atgatcgtgg    7740
tatgatcgtg ccttgttagg aaggcaacag acgggtctaa cacggattgg acgaaccact    7800
gaattccgca ttgcagagat attgtattta gtgcctagc tcgatacaat aaacgccatt     7860
tgaccattca ccacattggt gtgcacctgg gttgatggcc ggaccgttga ttccctgacg    7920
actacgagca catgcatgaa gcagaaggct tcatttggtg accccgacgt gatcgttagg    7980
gaatagtggt cggccacagg cggcgtggcg atcctgtcct catccgtctc gcttattcgg    8040
ggagcggacg atgaccctag tagaggggc tgcggcttag gagggcagaa gctgagtggc     8100
gtcggaggga gccctactgc aggggccaa catacccta cgagaactca gagagtcgtt      8160
ggaagacggg aaggaagccc gacgactgag cggtccaccc caggcgtgat tccggttgct    8220
ctgcgtgatt ccggtcgccc ggtggatcaa gcatggaagc cgtcataaag gtgatttcgt    8280
ccgcgtgtaa gacctattgc gggaaaacct ctccttctaa gaaggaaata ggggctatgt    8340
tgtccctgtt acaaaaggaa gggttgctta cgtcccctc agacttatat tccccgtgg     8400 cctgggatcc cattaccgcg cgctctctc agcgggctat ggtacttgga aaatcggag      8460 agttaaaaac ctggggattg gttttgggg cattgaaggc ggctcgagat ccggtacctt     8520
caaatactac aagtgaaaag tgtttgctta acatgttttt tattatgatt aaaggaacaa    8580
aagagcacat tcacaagacc cattacatat gggtacaagg aaaacaattt gaatagtaat    8640
ataccatatt tgccaacata ccatgattga gtcaaagttt agggagaaat gtgaattata    8700 agattttat aatgcatctt taggaagtca ggaagagcct tgtagtatca ggaacacaga     8760
gaacaagcaa ttgccttgtc agcataggaa tggttggtga cagttgataa tttaatctga    8820
gagattttga gtgactaatt ctggagcagc ttggtcatac agatatctgg cttaattgga    8880
aggctgcatt tttccccat aaaccttctg ctgatgtatc aggttgcatt tttcagtgtg     8940
atgactcagt actgtgagtc caatttcatt cccttaagcc ttcatccatg agttaccagt    9000
attactctgt gtaaaggaaa agtgaattgc acctgttctc acagtgtaat ttctttctga    9060 tttttttct agattaagct ccagctttta tgaagtctgg atgcagcaga taacatactt     9120 ttcatttac ccctgatact acagtgctct gggtcttgtt ggaagggaca gagtttttca     9180
gctttcttct tgcggccgct tcgaatcatt tgcccggaga cagggagagg ctcttctgcg    9240
tgtagtggtt gtgcagagcc tcatgcatca cggagcatga aagacgttc ccctgctgcc     9300 atctgctctt gtccacggtc agtttggagt agaggaagaa ggagccgtcg gagtccagca    9360
cgggaggcgt ggtcttgtag ttgttctccg gctgcccatt gctctcccac tccacggcga    9420
tgtcgctggg atagaagcct ttgaccaggc aggtcaggct gacttggttc ttggtcagct    9480
catcccggga tgggggcagg gtgtaaacct gtggttctcg gggctgccct ttggctttgg    9540
agatggtttt ctcgatgggg gctgggaggg ctttgttgga gaccttgcac ttgtactcct    9600
tgccattcag ccagtcttgg tgcaggacgg tcaggacgct gaccacacga tacgtgctgt    9660
tgtactgctc ctcccgcggc tttgtcttgg cattatgaac ctccacgccg tccacgtacc    9720
agttgaactt gacctcaggg tcttcgtggc taacgtccac caccacgcat gtgacctcag    9780
```

```
gggtccggga gatcatgagg gtgtccttgg gttttggggg aagaggaag actgacggtc    9840
cccccaggag ttcaggtgct gggcacggtg ggcatgtgtg agttttgtca caagatttgg   9900
gctctgcttt cttgtccacc ttggtgttgc tgggcttgtg attcacgttg cagatgtagg   9960
tctgggtgcc caagctgctg gagggcacgg tcaccacgct gctgagggag tagagtcctg  10020
aggattgtag gacagccggg aaagtatgca cgccgctggt cagggcgcct gagttccacg  10080
acaccgtcac cggttcgggg aagtagtcct tgaccaggca gcccagggcc gctgtgcccc  10140
cagaggtgct cttggaggag ggtgccaggg ggaagaccga tgggcccttg gtgctagctg  10200
cagagacggt gaccgtggtc cctgcgcccc agacattgaa gtaccagtca ccgccgtagt  10260
aagtcgatct tgcacagtaa tagaccgcag agtcctcaga tgtcaggctg ctgagttgca  10320
tgtaggctgt gctggaggat ttgtctgcag tcaatgtggc cttgcctttg aacttctgat  10380
tgtaggaagt atcaccattt ccgggataaa tagctccaat ccattccagg ccccgaccag  10440
gtgtctgttt tacccagtgc atattgtaac tggtaaatgt gtagccagaa gccttgcagg  10500
acatcttcac tgaggcccca ggcttcacca gctccgcccc cggctgctgc agttgtactt  10560
gggacaggac acgcgtagca acagcgacaa ggaagagcaa gatgaggctc caacccatgg  10620
ttgtggccat attatcatcg tgtttttcaa ggaaaaacca cgtccccgtg gttcgggggg  10680
cctagacgtt ttttaacctc gactaaacac atgtaaagca tgtgcaccga ggccccagat  10740
cagatcccat acaatggggt ac                                            10762
```

<210> SEQ ID NO 7
<211> LENGTH: 5109
<212> TYPE: DNA
<213> ORGANISM: Artificial
<220> FEATURE:
<223> OTHER INFORMATION: SBC201 B in pUC57 (IDT)

<400> SEQUENCE: 7

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ccgcccctct ccctcccccc    420
cccctaacgt tactggccga agccgcttgg aataaggccg gtgtgcgttt gtctatatgt    480
tattttccac catattgccg tcttttggca atgtgagggc ccggaaacct ggccctgtct    540
tcttgacgag cattcctagg ggtctttccc ctctcgccaa aggaatgcaa ggtctgttga    600
atgtcgtgaa ggaagcagtt cctctggaag cttcttgaag acaaacaacg tctgtagcga    660
ccctttgcag gcagcggaac ccccccacctg gcgacaggtg cctctgcggc caaaagccac    720
gtgtataaga tacacctgca aaggcggcac aaccccagtg ccacgttgtg agttggatag    780
ttgtggaaag agtcaaatgg ctctcctcaa gcgtattcaa caaggggctg aaggatgccc    840
agaaggtacc ccattgtatg ggatctgatc tggggcctcg gtgcacatgc tttacatgtg    900
tttagtcgag gttaaaaaac gtctaggccc cccgaaccac ggggacgtgg ttttcctttg    960
aaaaacacga tgataagctt gccacaacca tgggttggag cctcatcttg ctcttccttg   1020
tcgctgttgc tacgcgtgtc ctgtcccaag tacaactgca gcagccgggg gcggagctgg   1080
```

```
tgaagcctgg ggcctcagtg aagatgtcct gcaaggcttc tggctacaca tttaccagtt   1140
acaatatgca ctgggtaaaa cagacacctg gtcggggcct ggaatggatt ggagctattt   1200
atcccggaaa tggtgatact tcctacaatc agaagttcaa aggcaaggcc acattgactg   1260
cagacaaatc ctccagcaca gcctacatgc aactcagcag cctgacatct gaggactctg   1320
cggtctatta ctgtgcaaga tcgacttact acggcggtga ctggtacttc aatgtctggg   1380
gcgcagggac cacggtcacc gtctctgcag ctagcaccaa gggcccatcg gtcttccccc   1440
tggcaccctc ctccaagagc acctctgggg gcacagcggc cctgggctgc ctggtcaagg   1500
actacttccc cgaaccggtg acggtgtcgt ggaactcagg cgccctgacc agcggcgtgc   1560
atacttcccc ggctgtccta caatcctcag gactctactc cctcagcagc gtggtgaccg   1620
tgccctccag cagcttgggc acccagacct acatctgcaa cgtgaatcac aagcccagca   1680
acaccaaggt ggacaagaaa gcagagccca atcttgtgac aaaaactcac acatgcccac   1740
cgtgcccagc acctgaactc ctggggggac cgtcagtctt cctcttcccc ccaaaaccca   1800
aggacaccct catgatctcc cggacccctg aggtcacatg cgtggtggtg gacgttagcc   1860
acgaagaccc tgaggtcaag ttcaactggt acgtggacgg cgtggaggtt cataatgcca   1920
agacaaagcc gcgggaggag cagtacaaca gcacgtatcg tgtggtcagc gtcctgaccg   1980
tcctgcacca agactggctg aatggcaagg agtacaagtg caaggtctcc aacaaagccc   2040
tcccagcccc catcgagaaa accatctcca aagccaaagg gcagccccga gaaccacagg   2100
tttacaccct gcccccatcc cgggatgagc tgaccaagaa ccaagtcagc ctgacctgcc   2160
tggtcaaagg cttctatccc agcgacatcg ccgtggagtg ggagagcaat gggcagccgg   2220
agaacaacta caagaccacg cctcccgtgc tggactccga cggctccttc ttcctctact   2280
ccaaactgac cgtggacaag agcagatggc agcagggaa cgtcttctca tgctccgtga   2340
tgcatgaggc tctgcacaac cactacacgc agaagagcct ctccctgtct ccgggcaaat   2400
gattcgaagc ggccgcaaga agaaagctga aaaactctgt cccttccaac aagacccaga   2460
gcactgtagt atcaggggta aaatgaaaag tatgttatct gctgcatcca gacttcataa   2520
aagctggagc ttaatctaga aaaaaaatca gaaagaaatt acactgtgag aacaggtgca   2580
attcactttt cctttacaca gagtaatact ggtaactcat ggatgaaggc ttaagggaat   2640
gaaattggac tcacagtact gagtcatcac actgaaaaat gcaacctgat acatcagcag   2700
aaggtttatg ggggaaaaat gcagccttcc aattaagcca gatatctgta tgaccaagct   2760
gctccagaat tagtcactca aaatctctca gattaaatta tcaactgtca ccaaccattc   2820
ctatgctgac aaggcaattg gggcccgtcg actgcagagg cctgcatgca agcttggcgt   2880
aatcatggtc atagctgttt cctgtgtgaa attgttatcc gctcacaatt ccacacaaca   2940
tacgagccgg aagcataaag tgtaaagcct ggggtgccta atgagtgagc taactcacat   3000
taattgcgtt gcgctcactg cccgctttcc agtcgggaaa cctgtcgtgc cagctgcatt   3060
aatgaatcgg ccaacgcgcg gggagaggcg gtttgcgtat tgggcgctct tccgcttcct   3120
cgctcactga ctcgctgcgc tcggtcgttc ggctgcggcg agcggtatca gctcactcaa   3180
aggcggtaat acggttatcc acagaatcag gggataacgc aggaaagaac atgtgagcaa   3240
aaggccagca aaaggccagg aaccgtaaaa aggccgcgtt gctggcgttt ttccataggc   3300 tccgccccc tgacgagcat cacaaaaatc gacgctcaag tcagaggtgg cgaaacccga   3360
caggactata aagataccag gcgtttcccc ctggaagctc cctcgtgcgc tctcctgttc   3420
```

```
cgaccctgcc gcttaccgga tacctgtccg ccttctctcc ttcgggaagc gtggcgcttt    3480
ctcatagctc acgctgtagg tatctcagtt cggtgtaggt cgttcgctcc aagctgggct    3540
gtgtgcacga accccccgtt cagcccgacc gctgcgcctt atccggtaac tatcgtcttg    3600
agtccaaccc ggtaagacac gacttatcgc cactggcagc agccactggt aacaggatta    3660
gcagagcgag gtatgtaggc ggtgctacag agttcttgaa gtggtggcct aactacggct    3720
acactagaag aacagtattt ggtatctgcg ctctgctgaa gccagttacc ttcggaaaaa    3780
gagttggtag ctcttgatcc ggcaaacaaa ccaccgctgg tagcggtggt ttttttgttt    3840
gcaagcagca gattacgcgc agaaaaaaag gatctcaaga agatcctttg atcttttcta    3900
cggggtctga cgctcagtgg aacgaaaact cacgttaagg gattttggtc atgagattat    3960
caaaaaggat cttcacctag atccttttaa attaaaaatg aagttttaaa tcaatctaaa    4020
gtatatatga gtaaacttgg tctgacagtt accaatgctt aatcagtgag gcacctatct    4080
cagcgatctg tctatttcgt tcatccatag ttgcctgact ccccgtcgtg tagataacta    4140
cgatacggga gggcttacca tctggcccca gtgctgcaat gataccgcga gacccacgct    4200
caccggctcc agatttatca gcaataaacc agccagccgg aagggccgag cgcagaagtg    4260
gtcctgcaac tttatccgcc tccatccagt ctattaattg ttgccgggaa gctagagtaa    4320
gtagttcgcc agttaatagt ttgcgcaacg ttgttgccat tgctacaggc atcgtggtgt    4380
cacgctcgtc gtttggtatg gcttcattca gctccggttc ccaacgatca aggcgagtta    4440
catgatcccc catgttgtgc aaaaaagcgg ttagctcctt cggtcctccg atcgttgtca    4500
gaagtaagtt ggccgcagtg ttatcactca tggttatggc agcactgcat aattctctta    4560
ctgtcatgcc atccgtaaga tgcttttctg tgactggtga gtactcaacc aagtcattct    4620
gagaatagtg tatgcggcga ccgagttgct cttgcccggc gtcaatacgg gataataccg    4680
cgccacatag cagaacttta aaagtgctca tcattggaaa acgttcttcg ggcgaaaac     4740 tctcaaggat cttaccgctg ttgagatcca gttcgatgta acccactcgt gcacccaact    4800
gatcttcagc atcttttact ttcaccagcg tttctgggtg agcaaaaaca ggaaggcaaa    4860
atgccgcaaa aaagggaata agggcgacac ggaaatgttg aatactcata ctcttccttt    4920
ttcaatatta ttgaagcatt tatcagggtt attgtctcat gagcggatac atatttgaat    4980
gtatttagaa aaataaacaa ataggggttc cgcgcacatt tccccgaaaa gtgccacctg    5040
acgtctaaga aaccattatt atcatgacat taacctataa aaataggcgt atcacgaggc    5100
cctttcgtc                                                           5109

<210> SEQ ID NO 8
<211> LENGTH: 4091
<212> TYPE: DNA
<213> ORGANISM: Artificial
<220> FEATURE:
<223> OTHER INFORMATION: SBC201 A in pUC57 (IDT)

<400> SEQUENCE: 8
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctggc ttaactatgc ggcatcagag cagattgta ctgagagtgc      180 accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
```

```
tttcccagtc acgacgttgt aaaacgacgg ccagtgaatt ccaccacact ggactagtgg    420
atcctcaaca ctctcccctg ttgaagctct ttgtgacggg cgagctcagg ccctgatggg    480
tgacttcgca ggcgtagact ttgtgtttct cgtagtctgc tttgctcaga gtcagggtgc    540
tgctgaggct gtaggtgctg tccttgctgt cctgctctgt gacactctcc tgggagtttc    600
ccgattggag ggcgttatca accttccact gtactttggc ctctctggga tagaagttat    660
tcagcaggca cacaacagag gcagttccag atttcaactg ctcatcagat ggcgggaaga    720
tgaagacaga tggtgcagcc accgtacgtt tgatttccag cttggtcccc cctccgaacg    780
tgggtgggtt actagtccac tgctggcagt aataagtggc agcatcttca gcctccactc    840
tgctgattgt gagagagtaa aagtcccag acccactgcc actgaagcga cagggactc     900 cagaagccag gttggatgtg gcataaatcc aaggttttgg ggaggatcct ggcttttgct    960
ggaaccagtg gatgtaactg acacttgagc tggccctgca agtcattgtg accttctccc   1020
cgggagatgc agacaggatt gccggagatt gggagagaac aatttgtcct ctggacatta   1080
tgactgaagc actgattagc aggaagctga taatctgcac ctgaaaatcc atggtgaact   1140
ctgagttgtc tttcgagctt gactgctaaa ggcaatacag cttctagct gtatgtacag    1200 acactggctg agccctgggg aatatatagt ctgaattgtg acccacccac aggttccctt   1260
cagaagtttg accttttgaca ccatagaaat catttaatgg gattgggtta gattttagtt   1320
tcaataggtc cattttggat tgaatggaga gcaaatatta gttttttaatt ctgggtaaca   1380 atgtgttttc tgcctgttct gctaatccat caggactgtt ggatgggaga gaagactggg   1440
aaatattgct catgttccat tgagcttcag ttacaaccag ataatgggat ctttaagaaa   1500
acagaaaaat gtgggaacct tggagatgga aaacataatt agcaattatt agttagtgtg   1560
cttattacta tggttgtagt aacagaccag aagtctgttt catttgatcc ttcttgtatg   1620
tacaatgtgc atctgagcca cgctagacag gacataaatg agaacaagac ttgacctatt   1680
attttcttga caaaatagga gaaataaaga agcgtgcatg tgaaggagcc aactgagact   1740
agagtgaaga gcagacacac tttctttcct atagttggaa tatttaaatc tatctttta    1800 tgggtgtgaa tgctttataa cagggcccgt cgactgcaga ggcctgcatg caagcttggc   1860
gtaatcatgg tcatagctgt ttcctgtgtg aaattgttat ccgctcacaa ttccacacaa   1920
catacgagcc ggaagcataa agtgtaaagc ctggggtgcc taatgagtga gctaactcac   1980
attaattgcg ttgcgctcac tgcccgcttt ccagtcggga aacctgtcgt gccagctgca   2040
ttaatgaatc ggccaacgcg cggggagagg cggtttgcgt attgggcgct cttccgcttc   2100
ctcgctcact gactcgctgc gctcggtcgt tcggctgcgg cgagcggtat cagctcactc   2160
aaaggcggta atacggttat ccacagaatc aggggataac gcaggaaaga acatgtgagc   2220
aaaaggccag caaaaggcca ggaaccgtaa aaaggccgcg ttgctggcgt ttttccatag   2280
gctccgcccc cctgacgagc atcacaaaaa tcgacgctca agtcagaggt ggcgaaaccc   2340
gacaggacta taaagatacc aggcgtttcc ccctggaagc tccctcgtgc gctctcctgt   2400
tccgaccctg ccgcttaccg gatacctgtc cgcctttctc ccttcgggaa gcgtggcgct   2460
ttctcatagc tcacgctgta ggtatctcag ttcggtgtag gtcgttcgct ccaagctggg   2520
ctgtgtgcac gaaccccccg ttcagcccga ccgctgcgcc ttatccggta actatcgtct   2580
tgagtccaac ccggtaagac acgacttatc gccactggca gcagccactg gtaacaggat   2640
tagcagagcg aggtatgtag gcggtgctac agagttcttg aagtggtggc ctaactacgg   2700
```

| | |
|---|---|
| ctacactaga agaacagtat ttggtatctg cgctctgctg aagccagtta ccttcggaaa | 2760 |
| aagagttggt agctcttgat ccggcaaaca aaccaccgct ggtagcggtg gttttttgt | 2820 |
| ttgcaagcag cagattacgc gcagaaaaaa aggatctcaa gaagatcctt tgatcttttc | 2880 |
| tacgggtct gacgctcagt ggaacgaaaa ctcacgttaa gggattttgg tcatgagatt | 2940 |
| atcaaaaagg atcttcacct agatcctttt aaattaaaaa tgaagtttta atcaatcta | 3000 |
| aagtatatat gagtaaactt ggtctgacag ttaccaatgc ttaatcagtg aggcaccta | 3060 |
| ctcagcgatc tgtctatttc gttcatccat agttgcctga ctccccgtcg tgtagataac | 3120 |
| tacgatacgg gagggcttac catctggccc cagtgctgca atgataccgc gagacccacg | 3180 |
| ctcaccggct ccagatttat cagcaataaa ccagccagcc ggaagggccg agcgcagaag | 3240 |
| tggtcctgca actttatccg cctccatcca gtctattaat tgttgccggg aagctagagt | 3300 |
| aagtagttcg ccagttaata gtttgcgcaa cgttgttgcc attgctacag gcatcgtggt | 3360 |
| gtcacgctcg tcgtttggta tggcttcatt cagctccggt tcccaacgat caaggcgagt | 3420 |
| tacatgatcc cccatgttgt gcaaaaaagc ggttagctcc ttcggtcctc cgatcgttgt | 3480 |
| cagaagtaag ttggccgcag tgttatcact catggttatg gcagcactgc ataattctct | 3540 |
| tactgtcatg ccatccgtaa gatgcttttc tgtgactggt gagtactcaa ccaagtcatt | 3600 |
| ctgagaatag tgtatgcggc gaccgagttg ctcttgcccg gcgtcaatac gggataatac | 3660 |
| cgcgccacat agcagaactt taaaagtgct catcattgga aaacgttctt cggggcgaaa | 3720 |
| actctcaagg atcttaccgc tgttgagatc cagttcgatg taacccactc gtgcacccaa | 3780 |
| ctgatcttca gcatctttta ctttcaccag cgtttctggg tgagcaaaaa caggaaggca | 3840 |
| aaatgccgca aaaagggaa taagggcgac acggaaatgt tgaatactca tactcttcct | 3900 |
| ttttcaatat tattgaagca tttatcaggg ttattgtctc atgagcggat acatatttga | 3960 |
| atgtatttag aaaaataaac aaatagggt tccgcgcaca tttccccgaa aagtgccacc | 4020 |
| tgacgtctaa gaaaccatta ttatcatgac attaacctat aaaaataggc gtatcacgag | 4080 |
| gcccttcgt c | 4091 |

<210> SEQ ID NO 9
<211> LENGTH: 329
<212> TYPE: DNA
<213> ORGANISM: Artificial
<220> FEATURE:
<223> OTHER INFORMATION: synIRES3 090508

<400> SEQUENCE: 9

| | |
|---|---|
| ggtaccccat tgtatgggat ctgatctggg gcctcggtgc acatgcttta catgtgttta | 60 |
| gtcgaggtta aaaaacgtct aggccccccg aaccacgggg acgtggtttt cctttgaaaa | 120 |
| acacgatgat aatatggcca caaccatggg ttggagcctc atcttgctct tccttgtcgc | 180 |
| tgttgctacg cgtgtcctgt cccaagtaca actgcagcag ccgggggcgg agctggtgaa | 240 |
| gcctggggcc tcagtgaaga gtcctgcaa ggcttctggc tacacattta ccagttacaa | 300 |
| tatgcactgg gtaaaacaga cacctggtc | 329 |

AVIAN DERIVED ANTIBODIES

RELATED APPLICATION INFORMATION

This application claims the benefit of U.S. provisional patent application No. 61/217,138, filed May 27, 2009, the disclosure of which is incorporated in its entirety herein by reference.

FIELD OF THE INVENTION

The present invention relates to the expression of exogenous genetic material in avian cells. The invention also relates to transgenic avian species, including chicken, quail and turkey, and to avians which lay eggs containing exogenous proteins, for example pharmaceutical proteins including antibodies such as cytotoxic antibodies (e.g., anti-CD20) and to the exogenous proteins produced.

BACKGROUND

Recent developments in avian transgenesis have allowed the modification of avian genomes for exogenous protein production. Germ-line transgenic chickens can be produced by injecting replication-defective retrovirus into the subgerminal cavity of chick blastoderms in freshly laid eggs. See, for example, U.S. Pat. No. 7,511,120, issued Mar. 31, 2009, the disclosure of which is incorporated in its entirety herein by reference; issued U.S. Pat. No. 7,338,654, issued Mar. 4, 2008, the disclosure of which is incorporated in its entirety herein by reference; and US patent publication No. 2008/0064862 published Mar. 13, 2008, the disclosure of which is incorporated in its entirety herein by reference.

By weight, approximately 60% of an avian egg is composed of albumen which is composed of four major protein components; ovalbumin, ovomucoid, lysozyme and ovotransferrin with ovalbumin and ovomucoid being present in the greatest quantities. Use of regulatory sequences of genes which encode these proteins allows for expression of a heterologous gene product in the oviduct of a transgenic avian which is typically significantly advantageous over ubiquitous expression in the bird. That is, the consequences of ubiquitous expression of a bioactive gene product throughout the host animal is often undesirable. For example, in certain instances the ubiquitous presence of recombinant protein may be harmful to the development of the avian leading to death of the bird. Alternatively, the bird's health may be negatively effected leading to reduced levels of protein production.

Many currently accepted methods of producing therapeutic cytotoxic antibodies result in a less than optimum antibody dependent cellular cytotoxicity (ADCC) level of the antibody. What is needed are improved therapeutic antibodies including novel and improved forms of cytotoxic antibodies such as anti-CD20 antibodies.

SUMMARY OF THE INVENTION

The invention encompasses novel antibodies (e.g., cytotoxic antibodies) such as anti-CD20 antibodies produced in an avian, e.g., in an avian oviduct. In addition, the invention includes transgenic avians which produce eggs containing the recombinant antibody, progeny of the transgenic avians, methods of making the avians, the eggs containing the antibodies and isolating the antibodies.

In one particular aspect, the antibodies of the invention (e.g., cytotoxic antibodies) such as anti-CD20 are produced and glycosylated in an oviduct cell of the avian. For example, the antibody can be produced and glycosylated in a quail, chicken and turkey oviduct cell. In one embodiment, the antibody is produced and glycosylated in a tubular gland cell of the avian. The invention includes the avians (e.g., chicken, turkey and quail) that lay the eggs containing egg white which contains therapeutic protein molecules of the invention comprising one or more of the glycosylation structures disclosed herein.

Representative glycosylation structures have been determined for the antibody molecules (e.g., cytotoxic antibody molecules) such as anti-CD20 molecules (Anti-CD20) of the invention and are shown in FIGS. 1 and 2.

In one important aspect, the invention relates to an isolated mixture of antibody molecules (e.g., cytotoxic antibody molecules) such as anti-CD20 molecules comprising an antibody molecule of the invention glycosylated with at least one of the structures shown in FIGS. 1A, 1B and 2.

In one embodiment, the invention is directed to antibodies of the invention, such as anti-CD20 antibodies, glycosylated with a particular oligosaccharide structure chosen from those shown in FIGS. 1A, 1B and 2. For example, the invention can be directed to an anti-CD20 antibody glycosylated with the oligosaccharide structure shown at 1906.7 m/z of FIG. 2. In another example, the invention can be directed to an anti-CD20 antibody glycosylated with one or both of the oligosaccharide structures shown at 1620.7 m/z of FIG. 2. In one embodiment, the invention is directed to antibodies of the invention, such as anti-CD20 antibodies of the invention, glycosylated with two specific oligosaccharide structures chosen from those shown in FIGS. 1A, 1B and 2. In one embodiment, the invention is directed to antibodies of the invention, such as anti-CD20 antibodies of the invention, glycosylated with three specific oligosaccharide structures chosen from those shown in FIGS. 1A, 1B and 2. In one embodiment, the invention is directed to antibodies of the invention, such as anti-CD20 antibodies of the invention, glycosylated with four specific oligosaccharide structures chosen from those shown in FIGS. 1A, 1B and 2. In one embodiment, the invention is directed to antibodies of the invention, such as anti-CD20 antibodies of the invention, glycosylated with five or more specific oligosaccharide structures chosen from those shown in FIGS. 1A, 1B and 2, for example, 6, 7, 8, 9, 10, 11, 12, 13, 14, 15, 16, 17, 18 or more structures (e.g., all the structures) shown in FIGS. 1A, 1B and 2.

In one embodiment, the anti-CD20 molecules of an isolated mixture have the amino acid sequence shown in FIG. 3.

In one embodiment, the antibody molecules (e.g., cytotoxic antibody molecules) such as anti-CD20 molecules are in a pharmaceutical composition.

A potential glycosylation site for an anti-CD20 antibody of the invention is shown in FIG. 3. However, the invention is not limited to glycosylation at any particular site of the anti-CD20 antibody.

The invention is also directed to methods of treatment using the antibody molecules of the invention, (e.g., cytotoxic antibody molecules) such as anti-CD20, as is understood in the art. See, for example, U.S. Pat. No. 7,381,560, issued Jun. 3, 2008; U.S. Pat. No. 5,736,137, issued Apr. 7, 1998; U.S. Pat. No. 5,677,180, issued. Oct. 14, 1997; and U.S. Pat. No. 7,422,739, issued Sep. 9, 2008. The disclosure of each of these four patents is incorporated in its entirety herein by reference.

Anti-CD20 molecules of the invention are useful to destroy both normal and malignant B cells that have CD20 on their surfaces, and are therefore useful to treat diseases which are characterized by excess B cells, overactive B cells or dysfunctional B cells. Examples of indications that may be treated by administration of anti-CD20 antibodies of the invention include, but are not limited to, rheumatoid arthritis, multiple sclerosis, B cell lymphoma, polychondritis, mononeuritis multiplex, Alzheimer's disease, inflammatory bowel disease, systemic lupus erythematosis and anemias (such as autoimmune anemias) progressive multifocal leukoencephalopathy (PML) infection in SLE patients, idiopathic autoimmune hemolytic anemia, pure red cell aplasia, idiopathic thrombocytopenic purpura (ITP), Evans syndrome, vasculitis (for example Wegener's Granulomatosis), bullous skin disorders (for example pemphigus, pemphigoid), type 1 diabetes mellitus, Sjogren's syndrome and Devic's disease. It is also contemplated that antibodies of the invention can be used for anti-rejection treatment in organ transplant such as kidney transplant.

In one aspect, the invention is directed to antibody molecules (e.g., cytotoxic antibody molecules) such as anti-CD20 molecules obtained from a transgenic avian, for example, a transgenic chicken, which contains a transgene encoding the antibody. In one embodiment, the antibody molecules (e.g., cytotoxic antibody molecules) such as anti-CD20 molecules are produced in an avian oviduct cell, for example, a tubular gland cell. In one embodiment, the antibody molecules (e.g., cytotoxic antibody molecules) such as anti-CD20 molecules are contained in a hard shell egg, for example, a hard shell egg laid by an avian, for example, a chicken, which contains a transgene encoding the antibody molecules. For example, the antibody molecules may be present in the contents of an intact hard shell egg (e.g., in the egg white). The invention also includes egg white containing an antibody of the invention.

In one aspect, the invention is drawn to compositions containing antibody molecules (e.g., cytotoxic antibody molecules) such as anti-CD20 molecules produced in an avian (e.g., a transgenic chicken) which contains a transgene encoding the antibody molecules. In one embodiment, the antibody molecules in the composition are produced in an oviduct cell (e.g., a tubular gland cell) of a transgenic avian (e.g., transgenic chicken) and the molecules are isolated from egg white produced by the transgenic avian.

It is contemplated that the antibody molecules (e.g., cytotoxic antibody molecules) such as anti-CD20 molecules in a composition of the invention are N-glycosylated and/or O-glycosylated. In one embodiment, the antibody molecules (e.g., cytotoxic antibody molecules) such as anti-CD20 molecules in the composition are N-glycosylated and/or O-glycosylated in the oviduct cell (e.g., tubular gland cell) of the bird, for example, a chicken.

In one aspect, the invention relates to a composition, for example, a pharmaceutical composition, containing isolated antibody molecules of the invention having an avian derived glycosylation pattern. In one aspect, the invention relates to a composition, for example, a pharmaceutical composition, containing isolated antibody molecules (e.g., cytotoxic antibody molecules) such as anti-CD20 molecules, having an avian or poultry derived glycosylation pattern. In one aspect, the invention relates to a composition, for example, a pharmaceutical composition, containing isolated and glycosylated antibody molecules (e.g., cytotoxic antibody molecules) such as anti-CD20 molecules, produced in accordance with the invention.

In one embodiment, antibody molecules (e.g., cytotoxic antibody molecules) such as anti-CD20 molecules in compositions of the invention contain a glycosylation pattern other than that of antibody molecules (e.g., cytotoxic antibody molecules) such as anti-CD20 molecules produced in a mammalian cell. In one embodiment, antibody molecules (e.g., cytotoxic antibody molecules) such as anti-CD20 molecules in compositions of the invention contain a glycosylation pattern other than that of antibody molecules (e.g., cytotoxic antibody molecules) such as anti-CD20 molecules produced in a CHO cell.

In one embodiment, antibody molecules (e.g., cytotoxic antibody molecules) such as anti-CD20 molecules of the invention are attached to one or more N-linked oligosaccharide structures disclosed herein (e.g., those shown in Example 5). In one embodiment, antibody molecules (e.g., cytotoxic antibody molecules) such as anti-CD20 molecules of the invention are attached to one or more O-linked oligosaccharide structures disclosed in US patent publication No. 2009/0074718, published Mar. 19, 2009, the disclosure of which is incorporated in its entirety herein by reference.

One aspect of the present invention relates to avian hard shell eggs (e.g., chicken hard shell eggs) which contain an antibody of the invention including, but not limited to, a pharmaceutical antibody. The antibody in the egg is encoded by a transgene of a transgenic avian. The antibody may be present in an egg laid by the avian in any useful amount. In one embodiment, the antibody of the invention is present in an amount in a range of between about 0.01 µg per hard-shell egg and about 1 gram per hard-shell egg. In another embodiment, the antibody is present in an amount in a range of between about 1 µg per hard-shell egg and about 1 gram per hard-shell egg. For example, the antibody may be present in an amount in a range of between about 10 µg per hard-shell egg and about 1 gram per hard-shell egg (e.g., a range of between about 10 µg per hard-shell egg and about 400 mg per hard-shell egg).

In one embodiment, the antibody of the invention, for example, the pharmaceutical antibody (e.g., a cytotoxic antibody such as anti-CD20) is present in the egg white of the egg. In one embodiment, the antibody is present in an amount in a range of between about 1 ng per ml of egg white and about 0.2 gram per ml of egg white. For example, the antibody may be present in an amount in a range of between about 0.1 µg per ml of egg white and about 0.2 gram per ml of egg white (e.g., the antibody may be present in an amount in a range of between about 1 µg per ml of egg white and about 100 mg per ml of egg white. In one embodiment, the antibody is present in an amount in a range of between about 1 µg per ml of egg white and about 50 mg per ml of egg white. For example, the antibody may be present in an amount in a range of between about 1 µg per ml of egg white and about 10 mg per ml of egg white (e.g., the antibody may be present in an amount in a range of between about 1 µg per ml of egg white and about 1 mg per ml of egg white). In one embodiment, the antibody is present in an amount of more than 0.1 µg per ml of egg white. In one embodiment, the antibody is present in an amount of more than 0.5 µg per ml of egg white. In one embodiment, the antibody is present in an amount of more than 1 µg per ml of egg white. In one embodiment, the antibody is present in an amount of more than 1.5 µg per ml of egg white.

The avians developed from the blastodermal cells into which a vector containing a transgene encoding an antibody of the invention has been introduced are the G0 generation and can be referred to as "founders". Founder birds are typically chimeric for each inserted transgene. That is, only some of the cells of the G0 transgenic bird contain the transgene(s). The G0 generation typically is also hemizygous for the transgene(s). The G0 generation may be bred to non-transgenic animals to give rise to G1 transgenic offspring which are also hemizygous for the transgene and contain the transgene(s) in essentially all of the bird's cells. The G1 hemizygous offspring may be bred to non-transgenic animals giving rise to G2 hemizygous offspring or may be bred together to give rise to G2 offspring homozygous for the transgene. Substantially all of the cells of birds which are positive for the transgene that are derived from G1 offspring will contain the transgene(s). In one embodiment, hemizygotic G2 offspring from the same line can be bred to produce G3 offspring homozygous for the transgene. In one embodiment, hemizygous G0 animals are bred together to give rise to homozygous 01 offspring containing two copies of the transgene(s) in each cell of the animal. These are merely examples of certain useful breeding methods and the present invention contemplates the employment of any useful breeding method such as those known to individuals of ordinary skill in the art.

The invention also provides for compositions which contain isolated mixtures of an individual type of useful antibody molecule, such as those antibodies disclosed herein, where one or more of the antibody molecules contained in the mixture has a specific oligosaccharide structure attached, in particular, an oligosaccharide structure disclosed herein which may be produced by a transgenic avian.

Amino acids sequences within the scope of the invention include those sequences having a nucleotide sequence 80% identical and 85% identical and 90% identical and 91% identical and 92% identical and 93% identical and 94% identical and 95% identical and 96% identical and 97% identical and 98% identical and 99% identical to each of the sequences disclosed herein such as the sequences disclosed in FIGS. 3, 4 and 5. Nucleotide coding sequences for such amino acid sequences are also within the scope of the invention.

Nucleotide sequences also within the scope of the invention include those sequences having a nucleotide sequence 80% identical and 85% identical and 90% identical and 91% identical and 92% identical and 93% identical and 94% identical and 95% identical and 96% identical and 97% identical and 98% identical and 99% identical to each of the nucleotide sequences disclosed herein, such as those in the accompanying Sequence Listing.

Any useful combination of features described herein is included within the scope of the present invention provided that the features included in any such combination are not mutually inconsistent as will be apparent from the context, this specification, and the knowledge of one of ordinary skill in the art.

Additional objects and aspects of the present invention will become more apparent upon review of the detailed description set forth below when taken in conjunction with the accompanying figures, which are briefly described as follows.

BRIEF DESCRIPTION OF THE DRAWINGS

FIG. 3 shows the light chain (SEQ ID NO: 1) and heavy chain (SEQ ID NO: 2) amino acid sequences of anti-CD20 antibody made in accordance with the invention. The signal sequences which are cleaved are in italics and underlined. Glycosylation site is underlined and in bold. Terminal arginine of the heavy chain is encoded but may be removed from some or all of the antibodies during post-translational processing.

FIG. 4 shows the amino acid sequence of a single chain anti-CD20 molecule (SEQ ID NO: 3) that can be produced in accordance with the invention.

FIG. 5 shows a heavy chain (SEQ ID NO: 4) and light chain (SEQ ID NO: 5) of C2H7 antibody contemplated for production in accordance with the invention.

DEFINITIONS

Figure 1A:
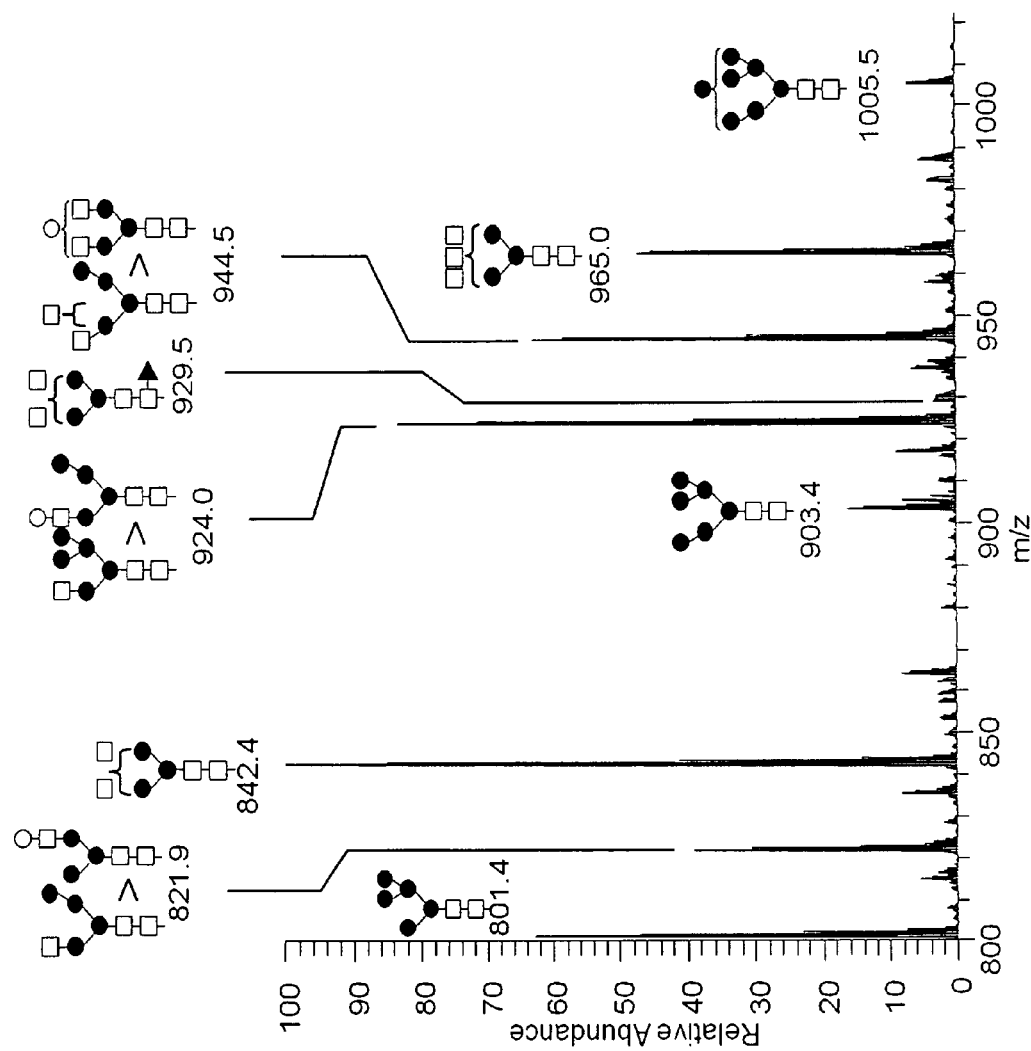
FIGS. 1A and 1B show N-glycans present on anti-CD20 antibodies produced in accordance with the invention identified by nanospray ionization (NSI). Square =N-acetylglucosamine; Circle =Galactose; Filled Triangle =Fucose; and Filled Circle =Mannose.

Certain definitions are set forth herein to illustrate and define the meaning and scope of the various terms used to describe the invention herein.

A "nucleic acid or polynucleotide sequence" includes, but is not limited to, eukaryotic mRNA, cDNA, genomic DNA, and synthetic DNA and RNA sequences, comprising the natural nucleoside bases adenine, guanine, cytosine, thymidine, and uracil. The term also encompasses sequences having one or more modified bases.

The term "avian" as used herein refers to any species, subspecies or race of organism of the taxonomic class ayes, such as, but not limited to chickens, quails, turkeys, ducks, geese, pheasants, parrots, finches, hawks, crows and ratites including ostrich, emu and cassowary. The term includes the various known strains of Gallus gallus, or chickens, (for example, White Leghorn, Brown Leghorn, Barred-Rock, Sussex, New Hampshire, Rhode Island, Australorp, Minorca, Amrox, California Gray), as well as strains of turkeys, pheasants, quails, duck, ostriches and other poultry commonly bred in commercial quantities. Avian also includes an individual avian organism in all stages of development, including embryonic and fetal stages.

A "cytotoxic antibody" after targeting and binding to an antigen triggers lysis and/or death of the cell expressing the antigen to which the cytotoxic antibody has bound.

"Anti-CD20" is an antibody that selectivity binds to the extracellular domain of the human CD20 antigen. Rituxan® is a commercially available anti-CD20.

Nucleic acid "control sequences" or "regulatory sequences" refer to promoter sequences, translational start and stop codons, ribosome binding sites, polyadenylation signals, transcription termination sequences, upstream regulatory domains, enhancers, and the like, as necessary and sufficient for the transcription and translation of a given coding sequence in a defined host cell. Examples of control sequences suitable for eukaryotic cells are promoters, polyadenylation signals, and enhancers. All of these control sequences need not be present in a recombinant vector so long as those necessary and sufficient for the transcription and translation of the desired coding sequence are present.

"Operably or operatively linked" refers to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "heterologous" and "exogenous" as they relate to nucleic acid sequences such as coding sequences and control sequences, denote sequences that are not normally associated with a region of a recombinant construct or with a particular chromosomal locus, and/or are not normally associated with a particular cell. Thus, an "exogenous" region of a nucleic acid construct is an identifiable segment of nucleic acid within or attached to another nucleic acid molecule that is not found in association with the other molecule in nature. For example, an exogenous region of a construct could include a coding sequence flanked by sequences not found in association with the coding sequence in nature. Another example of an exogenous coding sequence is a construct where the coding sequence itself is not found in nature (e.g., synthetic sequences having codons different from the native gene). Similarly, a host cell transformed with a construct or nucleic acid which is not normally present in the host cell would be considered exogenous to the cell.

As used herein the terms "oligosaccharide", "oligosaccharide pattern", "oligosaccharide structure", "carbohydrate chain", "glycosylation pattern" and "glycosylation structure" can have essentially the same meaning and refer to one or more structures which are formed from sugar residues and are attached to proteins of the invention.

"Exogenous protein" as used herein refers to a protein not naturally present in a particular tissue or cell and is the expression product of an exogenous expression construct or transgene, and/or a protein not naturally present in a given quantity in a particular tissue or cell. A protein that is exogenous to an egg is a protein that is not normally found in the egg. For example, a protein exogenous to an egg may be a protein that is present in the egg as a result of the expression of an exogenous or heterologous coding sequence present in a transgene of the animal laying the egg.

"Endogenous nucleotide sequence" refers to a naturally occurring nucleotide sequence or fragment thereof normally associated with a particular cell.

Figure 1B:
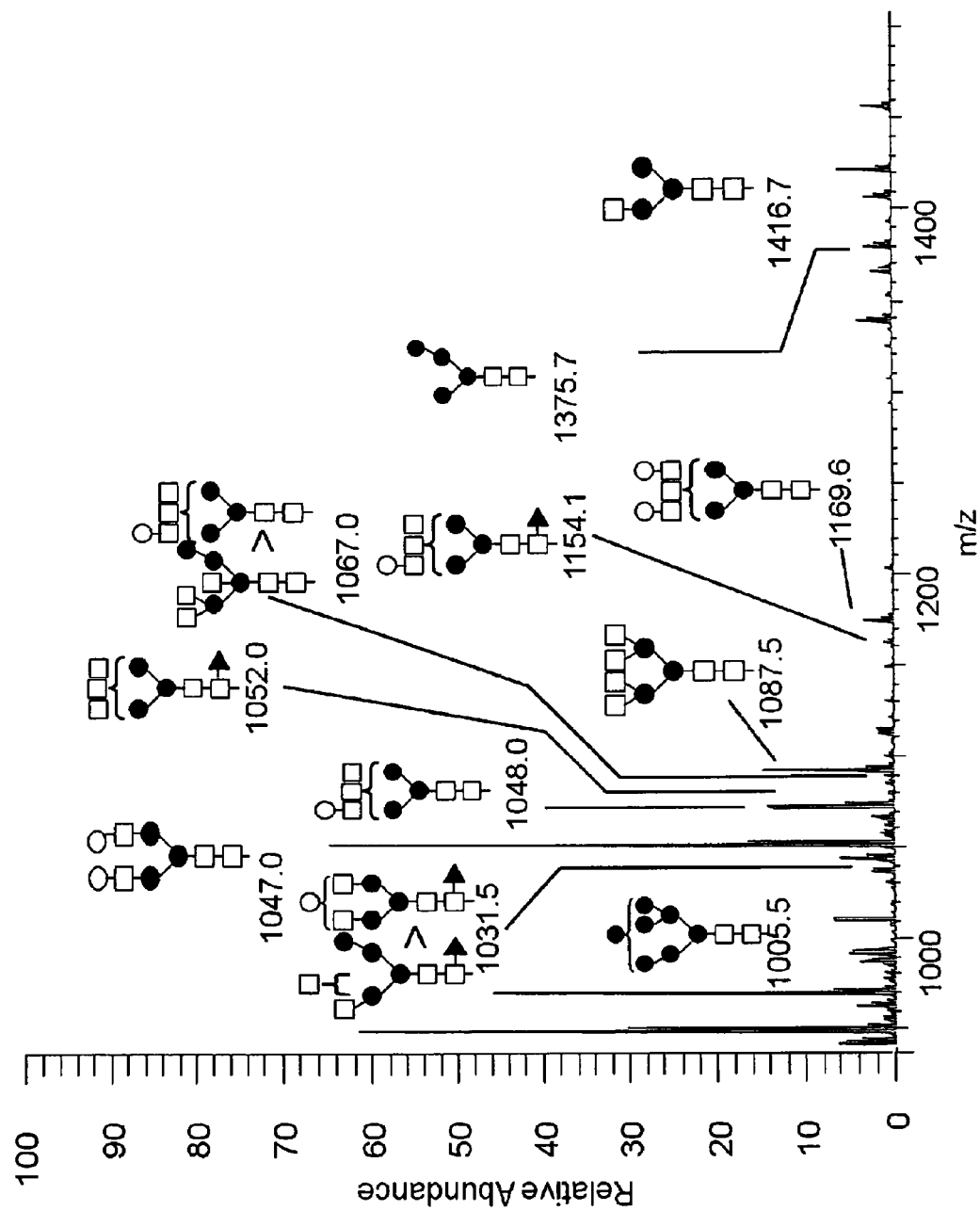
Figure 2:
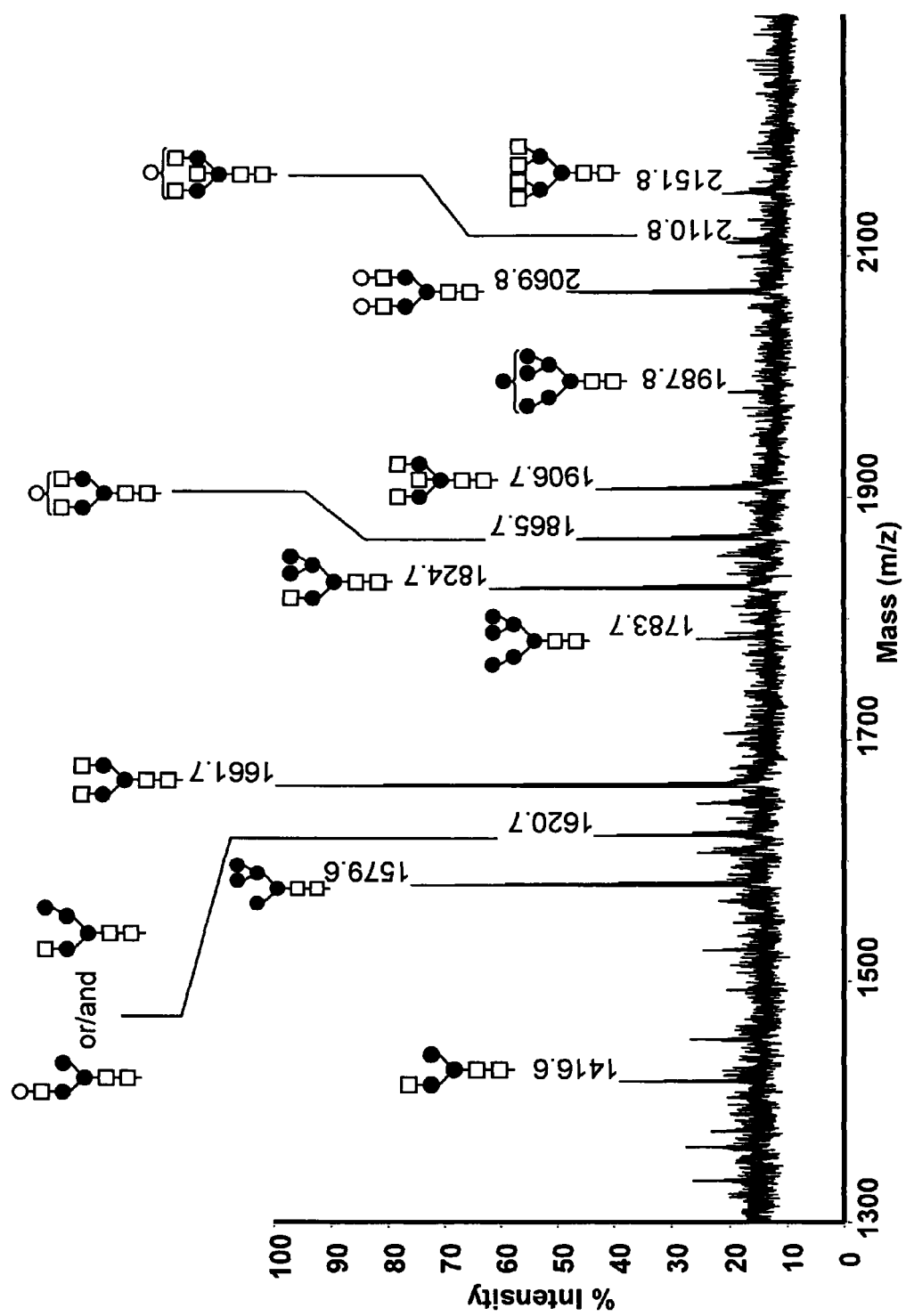
FIG. 2 shows N-glycans present on anti-CD20 antibodies produced in accordance with the invention identified by MALDI-TOF-MS. Square=N-acetylglucosamine; Circle=Galactose; Filled Triangle=Fucose; and Filled Circle=Mannose.

Each of the glycosylation structures shown in FIGS. 1 and 2 is an "oligosaccharide structure type" of the invention.

"Vector" means a polynucleotide comprised of single strand, double strand, circular, or supercoiled DNA or RNA. A typical vector may be comprised of one or more the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. The nucleic acid cassette can include a restriction site for insertion of the nucleic acid sequence to be expressed. In a functional vector the nucleic acid cassette typically contains the nucleic acid sequence to be expressed including translation, initiation and termination sites. An intron optionally may be included in the construct, for example, 5' to the coding sequence. A vector is constructed so that the particular coding sequence is located in the vector with the appropriate regulatory sequences, the positioning and orientation of the coding sequence with respect to the control sequences being such that the coding sequence is transcribed under the "control" of the control sequences or regulatory sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. In one embodiment, the coding sequence is cloned directly into an expression vector which already contains the control sequences and an appropriate restriction site which is in reading frame with and under regulatory control of the control sequences.

A "promoter" is a site on the DNA to which RNA polymerase binds to initiate transcription of a gene. In some embodiments the promoter will be modified by the addition or deletion of sequences, or replaced with alternative sequences, including natural and synthetic sequences as well as sequences which may be a combination of synthetic and natural sequences. Many eukaryotic promoters contain two types of recognition sequences: the TATA box and the upstream promoter elements. The former, located upstream of the transcription initiation site, is involved in directing RNA polymerase to initiate transcription at the correct site, while the latter appears to determine the rate of transcription and is upstream of the TATA box. Enhancer elements can also stimulate transcription from linked promoters, but many function exclusively in a particular cell type. Many enhancer/promoter elements derived from viruses, e.g., the SV40 promoter, the cytomegalovirus (CMV) promoter, the rous-sarcoma virus (RSV) promoter, and the murine leukemia virus (MLV) promoter are all active in a wide array of cell types, and are termed "ubiquitous". In one embodiment, non-constitutive promoters such as the mouse mammary tumor virus (MMTV) promoter are used in the present invention. The nucleic acid sequence inserted in the cloning site may have any open reading frame encoding a polypeptide of interest, with the proviso that where the coding sequence encodes a polypeptide of interest, it should preferably lack cryptic splice sites which can block production of appropriate mRNA molecules and/or produce aberrantly spliced or abnormal mRNA molecules.

The term "poultry derived" refers to a composition or substance produced by or obtained from poultry. "Poultry" refers to birds that can be kept as livestock, including but not limited to, chickens, duck, turkey, quail and ratites. For example, "poultry derived" may refer to chicken derived, turkey derived and/or quail derived.

A "retroviral particle", "transducing particle", or "transduction particle" refers to a replication-defective or replication-competent virus capable of transducing non-viral DNA or RNA into a cell.

The terms "transformation", "transduction" and "transfection" all denote the introduction of a polynucleotide into a cell such as an avian cell.

"Magnum" is that part of the oviduct between the infundibulum and the isthmus containing tubular gland cells that synthesize and secrete the egg white proteins of the egg. The term "oviduct cell" or "oviduct cells" as used herein can refer to magnum cell(s) and/or tubular gland cell(s).

Various methods of cloning, amplification, expression, and purification will be apparent to the skilled artisan. Representative methods are disclosed in Sambrook, Fritsch, and Maniatis, Molecular Cloning, a Laboratory Manual, 2nd Ed., Cold Spring Harbor Laboratory (1989).

DETAILED DESCRIPTION

The invention is directed to antibodies, such as anti-CD20 antibodies, produced transgenic avian oviduct tissue. For example, FIG. 3 shows the amino acid 25 sequence of an anti-CD20 antibody of the invention. Other examples of anti-CD20 antibodies which are included within the scope of the invention include, without limitation, ZEVALIN™ (Ibritumomab tiuxetan), BEXXAR® (Tositumomab) and C2H7, the sequence of which is shown in FIG. 5.

Shown in FIGS. 1A and 1B are oligosaccharide structures identified by NSI full-MS spectrum of permethylated N-glycans released, as is known in the art, from isolated anti-CD20 antibodies produced as disclosed herein, the heavy chain and light chain amino acid sequences of which are shown in FIG. 3.

As can be deduced from the relative peak heights of the spectrums shown in FIGS. 1A and 1B, the structures shown at 801.4 (structure 1), 821.9 (structure 2), 842.4 (structure 3), 924.0 (structure 4), 944.5 (structure 5), 965.0 (structure 6) and 1047.0 (structure 7) represent prevalent oligosaccharide structures. Accordingly, the invention includes compositions (e.g., egg white, pharmaceutical formulations) containing an antibody having one of structures 1 to 7. The invention also includes compositions containing 2 antibodies, each having a different attached oligosaccharide structure selected from structures 1 to 7. The invention also includes compositions containing 3 antibodies, each having a different attached oligosaccharide structure selected from structures 1 to 7. The invention also includes compositions containing 4 antibodies, each having a different attached oligosaccharide structure selected from structures 1 to 7. The invention also includes compositions containing 5 antibodies, each having a different attached oligosaccharide structure selected from structures 1 to 7. The invention also includes compositions containing 6 antibodies, each having a different attached oligosaccharide structure selected from structures 1 to 7. The invention also includes compositions containing 7 antibodies, each having a different attached oligosaccharide structure selected from structures 1 to 7.

FIG. 2 shows at least two additional oligosaccharide structures which were identified by MALDI/TOF-MS (1906.7 m/z and 2110.8 m/z) and which were not identified in the NSI-full MS spectrum analysis.

The invention encompasses compositions (e.g., egg white, pharmaceutical formulations) which contain anti-CD20 antibodies each having a single oligosaccharide attachment site in the Fc region of each polypeptide chain wherein the antibodies are glycosylated with oligosaccharide structures selected from FIGS. 1 and 2. The invention includes compositions (e.g., egg white, pharmaceutical formulations) containing an antibody having an attached oligosaccharide structure selected from the group shown in FIGS. 1 and 2. The invention also includes compositions containing 2 antibodies of the invention, each having a different attached oligosaccharide structure selected from the group shown in FIGS. 1 and 2. The invention also includes compositions containing 3 antibodies of the invention, each having a different attached oligosaccharide structure selected from the group shown in FIGS. 1 and 2. The invention also includes compositions containing 4 antibodies of the invention, each having a different attached oligosaccharide structure selected from the group shown in FIGS. 1 and 2. The invention also includes compositions containing 5 antibodies of the invention, each having a different attached oligosaccharide structure selected from the group shown in FIGS. 1 and 2. The invention also includes compositions containing 6 antibodies of the invention, each having a different attached oligosaccharide structure selected from the group shown in FIGS. 1 and 2. The invention also includes compositions containing 7 antibodies of the invention, each having a different attached oligosaccharide structure selected from the group shown in FIGS. 1 and 2. The invention also includes compositions containing 8 antibodies of the invention, each having a different attached oligosaccharide structure selected from the group shown in FIGS. 1 and 2. The invention also includes compositions containing 9 antibodies of the invention, each having a different attached oligosaccharide structure selected from the group shown in FIGS. 1 and 2. The invention also includes compositions containing 10 antibodies of the invention, each having a different attached oligosaccharide structure selected from the group shown in FIGS. 1 and 2. The invention also includes compositions containing 11 antibodies of the invention, each having a different attached oligosaccharide structure selected from the group shown in FIGS. 1 and 2. The invention also includes compositions containing 12 antibodies of the invention, each having a different attached oligosaccharide structure selected from the group shown in FIGS. 1 and 2. The invention also includes compositions containing 13 antibodies of the invention, each having a different attached oligosaccharide structure selected from the group shown in FIGS. 1 and 2. The invention also includes compositions containing 14 antibodies of the invention, each having a different attached oligosaccharide structure selected from the group shown in FIGS. 1 and 2. The invention also includes compositions containing 15 antibodies of the invention, each having a different attached oligosaccharide structure selected from the group shown in FIGS. 1 and 2. The invention also includes compositions containing 16 antibodies of the invention, each having a different attached oligosaccharide structure selected from the group shown in FIGS. 1 and 2. The invention also includes compositions containing 17 antibodies of the invention, each having a different attached oligosaccharide structure selected from the group shown in FIGS. 1 and 2. The invention also includes compositions containing 18 antibodies of the invention, each having a different attached oligosaccharide structure selected from the group shown in FIGS. 1 and 2. The invention also includes compositions containing 19 antibodies of the invention, each having a different attached oligosaccharide structure selected from the group shown in FIGS. 1 and 2. The invention also includes compositions containing 20 antibodies of the invention, each having a different attached oligosaccharide structure selected from the group shown in FIGS. 1 and 2. The invention also includes compositions containing 21 antibodies of the invention, each having a different attached oligosaccharide structure selected from the group shown in FIGS. 1 and 2. The invention also includes compositions containing 22 antibodies of the invention, each having a different attached oligosaccharide structure selected from the group shown in FIGS. 1 and 2. The invention also includes compositions containing 23 antibodies of the invention, each having a different attached oligosaccharide structure selected from the group shown in FIGS. 1 and 2. The invention also includes compositions containing 24 antibodies of the invention, each having a different attached oligosaccharide structure selected from the group shown in FIGS. 1 and 2. The invention also includes compositions containing 25 antibodies of the invention, each having a different attached oligosaccharide structure selected from the group shown in FIGS. 1 and 2. The invention also includes compositions containing 26 antibodies of the invention, each having a different attached oligosaccharide structure selected from the group shown in FIGS. 1 and 2. The invention also includes compositions containing 27 antibodies of the invention, each having a different attached oligosaccharide structure selected from the group shown in FIGS. 1 and 2. The invention also includes compositions containing 28 antibodies of the invention, each having a different attached oligosaccharide structure selected from the group shown in FIGS. 1 and 2. The invention also includes compositions containing 29 antibodies of the invention, each having a different attached oligosaccharide structure selected from the group shown in FIGS. 1 and 2. The invention also includes compositions containing 30 antibodies of the invention, each having a different attached oligosaccharide structure selected from the group shown in FIGS. 1 and 2. The invention also includes compositions containing 31 antibodies of the invention, each having a different attached oligosaccharide structure selected from the group shown in FIGS. 1 and 2. The invention also includes compositions containing 32 antibodies of the invention, each having a different attached oligosaccharide structure selected from the group shown in FIGS. 1 and 2. The invention also includes compositions containing 33 antibodies of the invention, each having a different attached oligosaccharide structure selected from the group shown in FIGS. 1 and 2. The invention also includes compositions containing 34 antibodies of the invention, each having a different attached oligosaccharide structure selected from the group shown in FIGS. 1 and 2. The invention also includes compositions containing 35 antibodies of the invention, each having a different attached oligosaccharide structure selected from the group shown in FIGS. 1 and 2. The invention also includes compositions containing 36 antibodies of the invention, each having a different attached oligosaccharide structure selected from the group shown in FIGS. 1 and 2. The invention also includes compositions containing 37 antibodies of the invention, each having a different attached oligosaccharide structure selected from the group shown in FIGS. 1 and 2.

In one aspect, the invention includes antibodies (e.g., cytotoxic antibodies) such as anti-CD20 antibodies wherein the antibodies have a poultry derived glycosylation pattern (e.g., poultry oviduct cell derived glycosylation pattern) such as a chicken, turkey or quail derived glycosylation pattern. In one aspect, the invention includes antibodies (e.g., cytotoxic antibodies) such as anti-CD20 antibodies wherein the antibodies have a transgenic avian derived glycosylation pattern (e.g., oviduct cell derived glycosylation pattern).

In one embodiment, the glycosylation pattern is other than that of the same antibody produced in a CHO cell. For example, the compositions can include an antibody (e.g., cytotoxic antibody) such as an anti-CD20 antibody with a poultry or avian derived carbohydrate chain (i.e., glycosylation structure) and that carbohydrate chain or glycosylation structure is not found on that antibody obtained from CHO cell production. However, the composition may also include an antibody (e.g., cytotoxic antibody) such as anti-CD20 that has one or more glycosylation structures that are the same as that found on the antibody when produced in CHO cells. That is, the mixture of antibody molecules (e.g., cytotoxic antibody molecules) such as anti-CD20 molecules may contain one or more antibody molecules having an oligosaccharide pattern which is disclosed herein and is not present when produced in CHO cells plus one or more antibody molecules having an oligosaccharide pattern which could be obtained in CHO cell production.

In one embodiment, the glycosylation pattern of an antibody (e.g., cytotoxic antibody) such as anti-CD20 produced in accordance with the invention is other than that of the antibody produced in mammalian cells. For example, the compositions can include an antibody (e.g., cytotoxic antibody) such as anti-CD20 molecule with a poultry or avian derived carbohydrate chain (i.e., glycosylation structure) and that carbohydrate chain or glycosylation structure is not found on that antibody obtained from mammalian cells. However, the composition may also include an antibody (e.g., cytotoxic antibody) such as anti-CD20 that has one or more glycosylation structures that are the same as that found on the antibody produced in mammalian cells. That is, the mixture of antibody molecules (e.g., cytotoxic antibody molecules) such as anti-CD20 molecules may contain one or more antibody molecules having an oligosaccharide pattern which is disclosed herein and is not present when produced in CHO cells plus one or more antibody molecules having an oligosaccharide pattern which could be obtained in mammalian cell production.

In one embodiment, provided for are antibodies of the invention (e.g., cytotoxic antibodies) such as anti-CD20 which are isolated. In one embodiment, the antibodies of the invention are contained in a composition are isolated. For example, the antibodies (e.g., cytotoxic antibodies) such as anti-CD20 may be isolated from egg white. The isolated antibodies may be antibody molecules that do not all have the same glycosylation structures among the antibody molecules or the isolated antibodies may be an isolated individual species of antibody molecules having only one particular glycosylation structure at a particular glycosylation site among the species of antibody molecules.

In one embodiment, at least about 5% of the N-linked oligosaccharides present on the antibody molecules (e.g., cytotoxic antibody molecules) such as anti-CD20 molecules of the invention contain fucose. In one embodiment, at least about 4% of the N-linked oligosaccharides present on the antibody molecules (e.g., cytotoxic antibody molecules) such as anti-CD20 molecules of the invention contain fucose. In one embodiment, at least about 3% of the N-linked oligosaccharides present on the antibody molecules (e.g., cytotoxic antibody molecules) such as anti-CD20 molecules of the invention contain fucose. In one embodiment, at least about 2% of the N-linked oligosaccharides present on the antibody molecules (e.g., cytotoxic antibody molecules) such as anti-CD20 molecules of the invention contain fucose. In one embodiment, at least about 1% of the N-linked oligosaccharides present on the antibody molecules (e.g., cytotoxic antibody molecules) such as anti-CD20 molecules of the invention contain fucose.

In one embodiment, some of the N-linked oligosaccharides present on the antibody molecules (e.g., cytotoxic antibody molecules) such as anti-CD20 molecules of the invention do not contain fucose. In one embodiment, about 90% or more of the N-linked oligosaccharides present on the antibody molecules (e.g., cytotoxic antibody molecules) such as anti-CD20 molecules of the invention do not contain fucose. In another embodiment, about 95% or more of the N-linked oligosaccharides present on the antibody molecules (e.g., cytotoxic antibody molecules) such as anti-CD20 molecules of the invention do not contain fucose. In another embodiment, about 96% or more of the N-linked oligosaccharides present on the antibody molecules (e.g., cytotoxic antibody molecules) such as anti-CD20 molecules of the invention do not contain fucose. In another embodiment, about 97% or more of the N-linked oligosaccharides present on the antibody molecules (e.g., cytotoxic antibody molecules) such as anti-CD20 molecules of the invention do not contain fucose. In another embodiment, about 98% or more of the N-linked oligosaccharides present on the antibody molecules (e.g., cytotoxic antibody molecules) such as anti-CD20 molecules of the invention do not contain fucose. In another embodiment, about 99% or more of the N-linked oligosaccharides present on the antibody molecules (e.g., cytotoxic antibody molecules) such as anti-CD20 molecules of the invention do not contain fucose. In one embodiment, the percentages in this paragraph refer specifically to the percentage of N-linked oligosaccharide structure present only on the Fc region that do not contain fucose.

In one embodiment, essentially none of the N-linked oligosaccharide structure types present on the antibody molecules (e.g., cytotoxic antibody molecules) such as anti-CD20 molecules of the invention contain fucose. In another embodiment, about 70% or more of the N-linked oligosaccharide structure types present on the antibody molecules (e.g., cytotoxic antibody molecules) such as anti-CD20 molecules of the invention do not contain fucose. In another embodiment, about 75% or more of the N-linked oligosaccharide structure types present on the antibody molecules (e.g., cytotoxic antibody molecules) such as anti-CD20 molecules of the invention do not contain fucose. In another embodiment, about 80% or more of the N-linked oligosaccharide structure types present on the antibody molecules (e.g., cytotoxic antibody molecules) such as anti-CD20 molecules of the invention do not contain fucose. In another embodiment, about 85% or more of the N-linked oligosaccharide structure types present on the antibody molecules (e.g., cytotoxic antibody molecules) such as anti-CD20 molecules of the invention do not contain fucose. In another embodiment, about 90% or more of the N-linked oligosaccharide structure types present on the antibody molecules (e.g., cytotoxic antibody molecules) such as anti-CD20 molecules of the invention do not contain fucose. In another embodiment, about 95% or more of the N-linked oligosaccharide structure types present on the antibody molecules (e.g., cytotoxic antibody molecules) such as anti-CD20 molecules of the invention do not contain fucose.

In one embodiment, some of the N-linked oligosaccharides present on the antibody molecules (e.g., cytotoxic antibody molecules) such as anti-CD20 molecules of the invention contain a bisecting GlcNAc. In one embodiment, about 2% or more of the N-linked oligosaccharides present on the antibody molecules (e.g., cytotoxic antibody molecules) such as anti-CD20 molecules of the invention contain a bisecting GlcNAc. In another embodiment, about 5% or more of the N-linked oligosaccharides present on the antibody molecules (e.g., cytotoxic antibody molecules) such as anti-CD20 molecules of the invention contain a bisecting GlcNAc. In another embodiment, about 10% or more of the N-linked oligosaccharides present on the antibody molecules (e.g., cytotoxic antibody molecules) such as anti-CD20 molecules of the invention contain a bisecting GlcNAc. In another embodiment, about 15% or more of the N-linked oligosaccharides present on the antibody molecules (e.g., cytotoxic antibody molecules) such as anti-CD20 molecules of the invention contain a bisecting GlcNAc. In another embodiment, about 20% or more of the N-linked oligosaccharides present on the antibody molecules (e.g., cytotoxic antibody molecules) such as anti-CD20 molecules of the invention contain a bisecting GlcNAc. In another embodiment, about 30% or more of the N-linked oligosaccharides present on the antibody molecules (e.g., cytotoxic antibody molecules) such as anti-CD20 molecules of the invention contain a bisecting GlcNAc. In one embodiment, the percentages in this paragraph refer specifically to the percentage of N-linked oligosaccharide structure present only on the Fc region that contain a bisecting GlcNAc.

In one embodiment, about 1% or more of the N-linked oligosaccharide structure types present on the antibody molecules (e.g., cytotoxic antibody molecules) such as anti-CD20 molecules of the invention contain a bisecting GlcNAc. In another embodiment, about 5% or more of the N-linked oligosaccharide structure types present on the antibody molecules (e.g., cytotoxic antibody molecules) such as anti-CD20 molecules of the invention contain a bisecting GlcNAc. In another embodiment, about 10% or more of the N-linked oligosaccharide structure types present on the antibody molecules (e.g., cytotoxic antibody molecules) such as anti-CD20 molecules of the invention contain a bisecting GlcNAc. In another embodiment, about 15% or more of the N-linked oligosaccharide structure types present on the antibody molecules (e.g., cytotoxic antibody molecules) such as anti-CD20 molecules of the invention contain a bisecting GlcNAc. In another embodiment, about 20% or more of the N-linked oligosaccharide structure types present on the antibody molecules (e.g., cytotoxic antibody molecules) such as anti-CD20 molecules of the invention contain a bisecting GlcNAc. In another embodiment, about 30% or more of the N-linked oligosaccharide structure types present on the antibody molecules (e.g., cytotoxic antibody molecules) such as anti-CD20 molecules of the invention contain a bisecting GlcNAc.

Without wishing to limit the invention to any particular theory or mechanism of operation it is believed that the presence of bisecting GlcNAc increases receptor binding (e.g., CFC receptor binding) providing for an increased activity or efficacy of the antibody.

In one embodiment, some of the N-linked oligosaccharides present on the antibody molecules (e.g., cytotoxic antibody molecules) such as anti-CD20 molecules of the invention are terminated partially or exclusively with N-acetyl glucosamine. In one embodiment, about 95% or more of the N-linked oligosaccharides present on the antibody molecules (e.g., cytotoxic antibody molecules) such as anti-CD20 molecules of the invention are terminated partially or exclusively with N-acetyl glucosamine. In another embodiment, about 90% or more of the N-linked oligosaccharides present on the antibody molecules (e.g., cytotoxic antibody molecules) such as anti-CD20 molecules of the invention are terminated partially or exclusively with N-acetyl glucosamine. In another embodiment, about 80% or more of the N-linked oligosaccharides present on the antibody molecules (e.g., cytotoxic antibody molecules) such as anti-CD20 molecules of the invention are terminated partially or exclusively with N-acetyl glucosamine. In another embodiment, about 70% or more of the N-linked oligosaccharides present on the antibody molecules (e.g., cytotoxic antibody molecules) such as anti-CD20 molecules of the invention are terminated partially or exclusively with N-acetyl glucosamine. In another embodiment, about 60% or more of the N-linked oligosaccharides present on the antibody molecules (e.g., cytotoxic antibody molecules) such as anti-CD20 molecules of the invention are terminated partially or exclusively with N-acetyl glucosamine. In another embodiment, about 50% or more of the N-linked oligosaccharides present on the antibody molecules (e.g., cytotoxic antibody molecules) such as anti-CD20 molecules of the invention are terminated partially or exclusively with N-acetyl glucosamine.

In one embodiment, all of the N-linked oligosaccharides structure types present on the antibody molecules (e.g., cytotoxic antibody molecules) such as anti-CD20 molecules of the invention are terminated partially or exclusively with N-acetyl glucosamine. In another embodiment, about 95% or more of the N-linked oligosaccharide structure types present on the antibody molecules (e.g., cytotoxic antibody molecules) such as anti-CD20 molecules of the invention are terminated partially or exclusively with N-acetyl glucosamine. In another embodiment, about 90% or more of the N-linked oligosaccharide structure types present on the antibody molecules (e.g., cytotoxic antibody molecules) such as anti-CD20 molecules of the invention are terminated partially or exclusively with N-acetyl glucosamine. In another embodiment, about 80% or more of the N-linked oligosaccharide structure types present on the antibody molecules (e.g., cytotoxic antibody molecules) such as anti-CD20 molecules of the invention are terminated partially or exclusively with N-acetyl glucosamine. In another embodiment, about 70% or more of the N-linked oligosaccharide structure types present on the antibody molecules (e.g., cytotoxic antibody molecules) such as anti-CD20 molecules of the invention are terminated partially or exclusively with N-acetyl glucosamine. In another embodiment, about 60% or more of the N-linked oligosaccharide structure types present on the antibody molecules (e.g., cytotoxic antibody molecules) such as anti-CD20 molecules of the invention are terminated partially or exclusively with N-acetyl glucosamine. In another embodiment, about 50% or more of the N-linked oligosaccharide structure types present on the antibody molecules (e.g., cytotoxic antibody molecules) such as anti-CD20 molecules of the invention are terminated partially or exclusively with N-acetyl glucosamine.

In one embodiment, the antibody (e.g., cytotoxic antibody) such as anti-CD20 is present in a hard shell egg. For example, the antibody may be present in the egg white of a hard shell egg laid by a transgenic avian of the invention. That is, in one embodiment, the invention is directed to avian (e.g., chicken) egg white containing an antibody of the invention. In one embodiment, the antibody (e.g., cytotoxic antibody) such as anti-CD20 is present in the egg white in an amount in excess of about 1 microgram per ml of egg white (e.g., present in an amount of about 1 microgram to about 0.5 gram per ml of egg white). For example, the antibody (e.g., cytotoxic antibody) such as anti-CD20 can be present in an amount greater than about 2 micrograms per ml of egg white (e.g., present in an amount of about 2 micrograms to about 200 micrograms per ml of egg white).

In one embodiment, the antibody, (e.g., cytotoxic antibody) such as anti-CD20 antibody, produced in accordance with the invention is produced as a single chain antibody, as is understood in the art. See, for example, Lee et al (1999) Molecular Immunology vol 36, p 61-71, the disclosure of which is incorporated in its entirety herein by reference, which discloses exemplary methodology useful for the design of a single chain antibody.

It is understood that though the reported method of making compositions of the invention is in avians, the compositions are not limited thereto. For example, certain of the glycosylated protein molecules of the invention may be produced in other organisms such as transgenic fish, transgenic plants, such as tobacco and duck weed (Lemna minor) or certain strains of yeast.

While it is possible that, for use in therapy, antibodies produced in accordance with this invention may be administered in raw form, it is preferable to administer the antibodies as part of a pharmaceutical composition.

One aspect of the invention relates to compositions containing antibody molecules (e.g., cytotoxic antibody molecules) such as anti-CD20 molecules produced in accordance with the invention. In a particularly useful embodiment, the antibody molecules (e.g., cytotoxic antibody molecules) such as anti-CD20 molecules are purified or isolated (e.g., isolated form egg white). For example, the antibody molecules can be removed from the contents of a hard shell egg (e.g., from the egg white) laid by a transgenic avian. In one embodiment, the antibody molecules (e.g., cytotoxic antibody molecules) such as anti-CD20 molecules of the invention have a glycosylation pattern resulting from the molecules being produced in an oviduct cell of an avian.

Another aspect of the invention relates to compositions containing antibody molecules (e.g., cytotoxic antibody molecules) such as anti-CD20 molecules produced in an avian oviduct cell (e.g., a tubular gland cell) that have a glycosylation pattern other than that of antibody molecules produced in a mammalian cell such as a CHO cell. In one aspect, the invention provides for compositions that contain isolated antibody molecules (e.g., cytotoxic antibody molecules) such as anti-CD20 molecules having an avian or poultry derived glycosylation pattern. For example, the compositions can contain a mixture of antibody molecules (e.g., cytotoxic antibody molecules) such as anti-CD20 molecules produced in avians, for example, chickens, in accordance with the invention and isolated from egg white. In one useful embodiment, the antibody molecules (e.g., cytotoxic antibody molecules) such as anti-CD20 molecules are in pharmaceutical compositions.

The invention provides for pharmaceutical compositions comprising poultry or avian derived glycosylated antibodies (e.g., cytotoxic antibodies) such as anti-CD20 together with one or more pharmaceutically acceptable carriers thereof and, optionally, other therapeutic and/or prophylactic ingredients and methods of administering such pharmaceutical compositions. The carrier(s) must be "acceptable" in the sense of being compatible with the other ingredients of the formulation and not deleterious to the recipient thereof. Methods of treating a patient (e.g., quantity of pharmaceutical protein administered, frequency of administration and duration of treatment period) using pharmaceutical compositions of the invention can be determined using standard methodologies known to physicians of skill in the art.

Pharmaceutical compositions include those suitable for oral, rectal, nasal, topical (including buccal and sub-lingual), vaginal or parenteral. The pharmaceutical compositions include those suitable for administration by injection including intramuscular, sub-cutaneous and intravenous administration. The pharmaceutical compositions also include those for administration by inhalation or insufflation. The compositions or formulations may, where appropriate, be conveniently presented in discrete dosage units and may be prepared by any of the methods well known in the art of pharmacy. The methods of producing the pharmaceutical compositions typically include the step of bringing the antibodies into association with liquid carriers or finely divided solid carriers or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste.

Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

Antibodies of the invention may also be formulated for parenteral administration (e.g., by injection, for example bolus injection or continuous infusion) and may be presented in unit dose form in ampoules, pre-filled syringes, small volume infusion or in multi-dose containers with an added preservative. The antibodies may be injected by, for example, subcutaneous injections, intramuscular injections, and intravenous infusions or injections.

The antibodies may take such forms as suspensions, solutions, or emulsions in oily or aqueous vehicles, and may contain formulatory agents such as suspending, stabilizing and/or dispersing agents. It is also contemplated that the antibodies may be in powder form, obtained by aseptic isolation of sterile solid or by lyophilization from solution, for constitution with a suitable vehicle, e.g., sterile, pyrogen-free water, before use.

For topical administration to the epidermis, the antibodies produced according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration wherein the carrier is a solid are most preferably represented as unit dose suppositories. Suitable carriers include cocoa butter and other materials commonly used in the art, and the suppositories may be conveniently formed by a mixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient, such carriers as are known in the art to be appropriate.

For intra-nasal administration the antibodies of the invention may be used as a liquid spray or dispersible powder or in the form of drops.

Drops may be formulated with an aqueous or non-aqueous base also comprising one or more dispersing agents, solubilizing agents or suspending agents. Liquid sprays are conveniently delivered from pressurized packs.

For administration by inhalation, antibodies according to the invention may be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

For administration by inhalation or insufflation, the antibodies according to the invention may take the form of a dry powder composition, for example a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient, may be employed.

The pharmaceutical compositions according to the invention may also contain other active ingredients such as antimicrobial agents, or preservatives.

It is contemplated that the antibodies of the invention may be used in combination with other therapeutic agents.

Compositions or compounds of the invention can be used to treat a variety of conditions. For example, there are many conditions for which treatment therapies are known to practitioners of skill in the art in which antibodies obtained from cell culture (e.g., CHO cells) are employed. The present invention contemplates that the glycosylated antibodies produced in an avian system can be employed to treat such conditions. That is, the invention contemplates the treatment of conditions known to be treatable by conventionally produced antibodies by using antibodies produced in accordance with the invention. For example, antibodies (e.g., cytotoxic antibodies) such as anti-CD20 produced in accordance with the invention can be used to treat human conditions, as understood in the art.

Generally, the dosage administered will vary depending upon known factors such as age, health and weight of the recipient, type of concurrent treatment, frequency of treatment, and the like. Usually, a dosage of active ingredient can be between about 0.0001 mg and about 10 mg per kilogram of body weight. Precise dosage, frequency of administration and time span of treatment can be determined by a physician skilled in the art of administration of the respective therapeutic protein.

By the methods of the present invention, transgenes can be introduced into avian embryonic blastodermal cells to produce a transgenic chicken, transgenic turkey, transgenic quail and other avian species, that carry a transgene in the genetic material of its germ-line tissue to produce proteins of the invention. The blastodermal cells are typically stage VII-XII cells, or the equivalent thereof, and in one embodiment are near stage X. The cells useful in the present invention include embryonic germ (EG) cells, embryonic stem (ES) cells & primordial germ cells (PGCs). The embryonic blastodermal cells may be isolated freshly, maintained in culture, or in a particularly useful embodiment, reside within an embryo.

Some vectors useful in carrying out the methods of the present invention are described herein. These vectors can be used for stable introduction of an exogenous coding sequence into the genome of an avian. The vectors may be used to produce proteins of the invention such as antibodies in specific tissues of an avian, for example, in the oviduct tissue of an avian. The vectors may also be used in methods to produce avian eggs which contain exogenous protein. In one embodiment, the coding sequence and the promoter are both positioned between 5' and 3' LTRs before introduction into blastodermal cells. In one embodiment, the vector is retroviral and the coding sequence and the promoter are both positioned between the 5' and 3' LTRs of the retroviral SIN vector. In one useful embodiment, the LTRs or retroviral vector is derived from the avian leukosis virus (ALV), murine leukemia virus (MLV), or lentivirus.

Useful retroviruses for introducing a transgene into the avian genome are the replication-deficient avian leucosis virus (ALV), the replication-deficient murine leukemia virus (MLV) and the lentivirus. Any of the vectors of the present invention may include a coding sequence encoding a signal peptide that will direct secretion of the protein expressed by the vector's coding sequence from the tubular gland cells of the oviduct. Where an exogenous protein would not otherwise be secreted, the vector containing the coding sequence is modified to comprise a DNA sequence encoding a useful signal peptide. The DNA sequence encoding the signal peptide is inserted in the vector such that it is located at the N-terminus of the protein encoded by the DNA. The signal peptide can direct secretion of the exogenous protein expressed by the vector into the egg white of a hard shell egg. The vector may include a marker gene, wherein the marker gene is operably linked to a promoter.

Any useful promoter can be employed. For example, the promoter can be a constitutive promoter such as a cytomegalovirus (CMV) promoter, a rous-sarcoma virus (RSV) promoter, a murine leukemia virus (MLV) promoter, a beta-actin promoter. The promoter can also be a magnum specific promoter such as an ovalbumin promoter, a lysozyme promoter, a conalbumin promoter, an ovomucoid promoter, an ovomucin promoter or an ovotransferrin promoter. Both constitutive and magnum specific promoters have proven suitable for expression of exogenous protein in the oviduct.

The methods of the invention which provide for the production of protein of the invention in the avian oviduct and the production of eggs which contain the exogenous protein involve an additional step subsequent to providing a suitable vector and introducing the vector into embryonic blastodermal cells so that the vector is integrated into the avian genome. The subsequent step involves deriving a mature transgenic avian from the transgenic blastodermal cells produced. Deriving a mature transgenic avian from the blastodermal cells typically involves transferring the vector into an embryo and allowing that embryo to develop fully, so that the transduced cells become incorporated into the avian as the embryo is allowed to develop. The resulting chick is then grown to maturity. In one embodiment, the cells of a blastodermal embryo are transfected or transduced with the vector directly within the embryo. The resulting embryo is allowed to develop and the chick allowed to mature.

The transgenic avian so produced from the transgenic blastodermal cells is known as a founder. Some founders will carry the transgene in the tubular gland cells in the magnum of their oviducts. These avians will express the exogenous protein encoded by the transgene in their oviducts. The exogenous protein may also be expressed in other tissues (e.g., blood) in addition to the oviduct. If the exogenous protein contains the appropriate signal sequence(s), it will be secreted into the lumen of the oviduct and into the egg white of the egg. Some founders are germ-line founders. A germ-line founder is a founder that carries the transgene in genetic material of its germ-line tissue, and may also carry the transgene in oviduct magnum tubular gland cells that express the exogenous protein. Therefore, in accordance with the invention, the transgenic avian will have tubular gland cells expressing the exogenous protein, and the offspring of the transgenic avian will also have oviduct magnum tubular gland cells that express the exogenous protein.

Other specific examples of therapeutic proteins which may be produced as disclosed herein include, without limitation, factor VIII, b-domain deleted factor VIII, factor VIIa, factor IX, anticoagulants, hirudin, alteplase, tpa, reteplase, tpa, tpa—3 of 5 domains deleted, insulin, insulin lispro, insulin aspart, insulin glargine, long-acting insulin analogs, hgh, glucagons, tsh, follitropin-beta, fsh, gm-csf, pdgh, ifn alpha2, ifn alpha2a, ifn alpha2b, ifn-alpha, ifn-beta 1b, ifn-beta, ifn-gamma1b, il-2, il-11, hbsag, ospa, murine mab directed against t-lymphocyte antigen, murine mab directed against tag-72, tumor-associated glycoprotein, fab fragments derived from chimeric mab directed against platelet surface receptor gpII(b)/III(a), murine mab fragment directed against tumor-associated antigen ca125, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, dornase-alpha dnase, beta glucocerebrosidase, tnf-alpha, il-2-diptheria toxin antibody, tnfr-lgg fragment antibody laronidase, dnaases, alefacept, darbepoetin alfa (colony stimulating factor), tositumomab, murine mab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, etanercept, antidiuretic hormones, prolactin and thyroid stimulating hormone.

The invention also includes the production of lysosomal acid lipase (LAL) produced in accordance with the invention. The amino acid sequence for human LAL is well known in the art, see, for example, Anderson, R. A. and Sando, G. N., "Cloning and Expression of cDNA Encoding Human Lysosomal Acid Lipase/Cholesteryl Ester Hydrolase", Journal of Biological Chemistry, Vol. 266, No. 33, Issue of November 25, pp. 22479-22484 (1991).

The invention also includes the production of glucocerebrosidase produced in accordance with the invention. Sequence information for human glucocerebrosidase is well known in the art, see, and, for example, Sorge, et al., "Molecular cloning and nucleotide sequence of human glucocerebrosidase cDNA", Proc. Natl. Acad. Sci, Vol 82, pp 7289-7293 (1985).

Certain antibodies which may be produced in accordance with the invention include, without limitation, Muromonab; Satumomab pendetide; mAb=B72.3, conjugate of B72.3 and radioligand=CYT 103; Abciximab; Edrecolomab, Mab 17-1A; murine Mab fragment directed against tumor-associated antigen CA 125; Arcitumomab; Imciromab pentetate Capromab pendetide; murine Mab fragments (Fab/Fab2 mix) directed against HMW-MAA; Nofetumomab; Sulesomab; chimeric Mab directed against CD20 antigen found on surface of B lymphocytes; Daclizumab; Basiliximab; Palivizumab; Trastuzumab; human Mab directed against bytokeratin tumor-associated antigen; Rituximab; Infliximab; Gemtuzumab ozogamicin; Alemtuzumab; Tositumomab (conjugated to 131I); Omalizumab; Ibritumomab tiuxetan (conjugated to 90Y); Efalizumab; Cetuximab; Bevacizumab; Adalimumab (IgG1); Technetium (99 mTc) fanolesomab; Natalizumab; Ranibizumab; Panitumumab; Eculizumab.

In one particularly useful embodiment, antibodies produced in accordance with the invention are produced in a single chain form. See, for example, Lee et al, Molecular Immunology (1999) vol 36, p 61-71 which discloses the production of single chain antibodies, the disclosure of which is incorporated in its entirety herein by reference. For example, any antibody which can be produced in accordance with the invention in single chain form, including but not limited to each of the antibodies specifically disclosed herein, is contemplated for production in a single chain form in a transgenic avian oviduct.

Certain enzymes, such as human enzymes, which can be produced in accordance with the invention include Rasburicase; Asparaginase; Urokinase; Tenecteplase; adenosin deaminase; Glucocerebrosidase; lysosomal acid lipase (Cholestrase); Palmitoyl-protein thioesterase 1; PPT1, B-Galactosidase; Neuraminidase; heparan sulfamidase; N-acetyl-glucosaminidase; alpha-N-acetylglucosaminidase; alpha-glucosaminide N-acetyltransferase; N-acetylglucosamine-6-sulfate sulfatase; galactosylceramidase (GALC); Glucoronidase; NPC1; NPC2; Agalsidase alfa; Agalsidase beta; alpha-glucosidase; Acid Sphingomyelinase (ASM); N-acetylgalactosamine 6-sulfatase (GALNS or galactose 6-sulfatase); beta-galactosidase; Idursulfase; alpha-L-duronidase; Galsulfase: arylsulfatase B, BM 102, arylsulfatase B, N-acetylgalactosamine-4-sulfatase, ASB.; lysosomal alpha-mannosidase (LAMAN); beta-hexosaminidase; alglucosidase alfa; beta-hexosaminidase A; tripeptidyl peptidase 1 (TPP 1).

Other protein therapeutics which can be produced in accordance with the invention include, without limitation, Factor VIII; B-domain deleted Factor VIII; Factor VIIa; Factor IX; anticoagulant; recombinant hirudin; anticoagulant; recombinant hirudin; Alteplase, tPA; Reteplase, human tPA-3 of 5 domains deleted; Factor XI; Factor XII (Hageman factor); Factor XIII; Alpha2-antiplasmin; Microplasmin; insulin lispro; Bio Lysprol, an insulin analog; insulin aspart; insulin glargine; long-acting insulin analog; hGH; glucagons; TSH; follitropin-beta FSH; salmon calcitonin; (Teriparatide) Parathyroid hormone derivative; nesiritide, B-type natriuretic peptide (BNP); PDGH; Lutropin alfa; Choriogonadotropin alfa; Somatropin Pegvisomant, human growth hormone receptor antagonist; platelet derived growth factor (PDGF); Keratinocyte growth factor; fibroblast growth factor 23; insulin-like growth factor-1, IGF-1 complexed with IGFBP-3; HBsAg; vaccine containing HBsAgn as one component; OspA, a lipoprotein found on the surface of $B$ $burgorferi$; Hep B-IPV HIB vaccine; Hep B-IPV vaccine; Comb vaccine; Pneumococcal conjugate vaccine; Influenza virus vaccine live, intranasal; Alefacept, Immunosuppressive agent; TNF-alpha; TNFR-IgG fragment antibody; Abatacept; recombinant activated protein C; dornase-alpha DNAse; Enfuvirtide (HIV fusion inhibitor) Anakinra, Botulinum Toxins, e.g., Type A; Samarium [153 m] lexidronam; Perfultren; Cetrorelix; Eptifibatide; Insulin Glargine; Insulin Aspart; Hepatitis B virus small surface antigen (HbsAg); Eptotermin alfa; Protein C; Inactivated hepatitis A virus hepatitis B surface antigen; Dibotermin alfa; IL-2-diptheria toxin antibody that targets cells displaying a surface IL-2 receptor; Endostatin; Human insulin-like growth factor binding protein-6.

The therapeutic proteins of the invention can be produced by methods such as those disclosed herein or by other such methods including those disclosed in US patent publication No. 2008/0064862, published Mar. 13, 2008.

The invention encompasses glycosylated antibody compositions of matter such as cytotoxic antibodies. For example, the invention includes the glycosylated composition of matter for anti-CD20; TNFR-Fc (e.g., TNF receptor type II-IgG, e.g., Enbrel); EPO-Fc (e.g., erythropoietin-Fc); GIRT-Fc (e.g., glucocorticoid induced tumor necrosis factor); cytotoxic IL-2/Fc as well as other cytotoxic antibodies.

The invention includes methods for producing multimeric proteins including immunoglobulins, such as antibodies, and antigen binding fragments thereof. Thus, in one embodiment of the present invention, the multimeric protein is an immunoglobulin, wherein the first and second heterologous polypeptides are immunoglobulin heavy and light chains respectively.

In certain embodiments, an immunoglobulin polypeptide encoded by the transcriptional unit of at least one expression vector may be an immunoglobulin heavy chain polypeptide comprising a variable region or a variant thereof, and may further comprise a D region, a J region, a C region, or a combination thereof. An immunoglobulin polypeptide encoded by an expression vector may also be an immunoglobulin light chain polypeptide comprising a variable region or a variant thereof, and may further comprise a J region and a C region. The present invention also contemplates multiple immunoglobulin regions that are derived from the same animal species, or a mixture of species including, but not only, human, mouse, rat, rabbit and chicken. In certain embodiments, the antibodies are human or humanized.

In other embodiments, the immunoglobulin polypeptide encoded by at least one expression vector comprises an immunoglobulin heavy chain variable region, an immunoglobulin light chain variable region, and a linker peptide thereby forming a single-chain antibody capable of selectively binding an antigen.

Some other examples of therapeutic antibodies that may be produced in methods of the invention include, but are not limited, to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glyco-protein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2an antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath; Campath 1H/LDP-03 which is a humanized anti-CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (CS) antibody (Alexion Pharm); D2E7 is a humanized anti-TNF-α antibody (CATIBASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); Ortho-Clone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); CAT-152, a human anti-TGF-$\beta_2$ antibody (Cambridge Ab Tech); Cetuximab (BMS) is a monoclonal anti-EGF receptor (EGFr) antibody; Bevacizuma (Genentech) is an anti-VEGF human monoclonal antibody; Infliximab (Centocore, JJ) is a chimeric (mouse and human) monoclonal antibody used to treat autoimmune disorders; Gemtuzumab ozogamicin (Wyeth) is a monoclonal antibody used for chemotherapy; and Ranibizumab (Genentech) is a chimeric (mouse and human) monoclonal antibody used to treat macular degeneration.

Proteins produced in transgenic avians in accordance with the invention can be purified from egg white by any useful procedure such as those apparent to a practitioner of ordinary skill in the art of protein purification. For example, the antibody molecules (e.g., cytotoxic antibody molecules) such as anti-CD20 molecules produced in transgenic avians in accordance with the invention can be purified from egg white by methods apparent to practitioners of ordinary skill in the art of protein purification. For example, cytotoxic containing antibodies of the invention may be isolated using a Protein A column.

The contents of all references, published patents and patents cited throughout the present application are hereby incorporated by reference in their entireties.

The following specific examples are intended to illustrate the invention and should not be construed as limiting the scope of the claims.

EXAMPLE 1

Construction of pSIN-OV-1.1-I-SBC201-I3

The vector pSIN-OV-3.5-I-CTLA4-inv disclosed in US patent publication No. 2008/0064862, filed Mar. 13, 2008, the disclosure of which was incorporated in its entirety herein by reference, was digested with AflII, filled in with Klenow and then cut with NruI. The resulting 9170 by fragment was isolated and self-ligated to create pSIN-OV-1.1-I-CTLA4-inv.

Coding sequences and flanking sequences for SBC201 were synthesized by IDT (Coralville, IA) and cloned into a PUC-based plasmid (pUC57) resulting in SBC201 B (SEQ ID NO: 7) and SBC201 A (SEQ ID NO: 8). The coding sequence of SBC201 B is represented by nucleotides 990 to 2402 of SEQ ID NO: 7. The coding sequence of SBC201 A is represented by nucleotides 425 to 1132 of SEQ ID NO: 8.

pSIN-OV-1.1-I-SBC201 was generated by ligation of the 7795 by NcoI/AflII fragment of pSIN-OV-1.1-I-CTLA4-inv to the 2234 by EcoRI/AflII fragment of SBC201B and the 733 by EcoRI/NcoI fragment of SBC201A.

Figure 9:
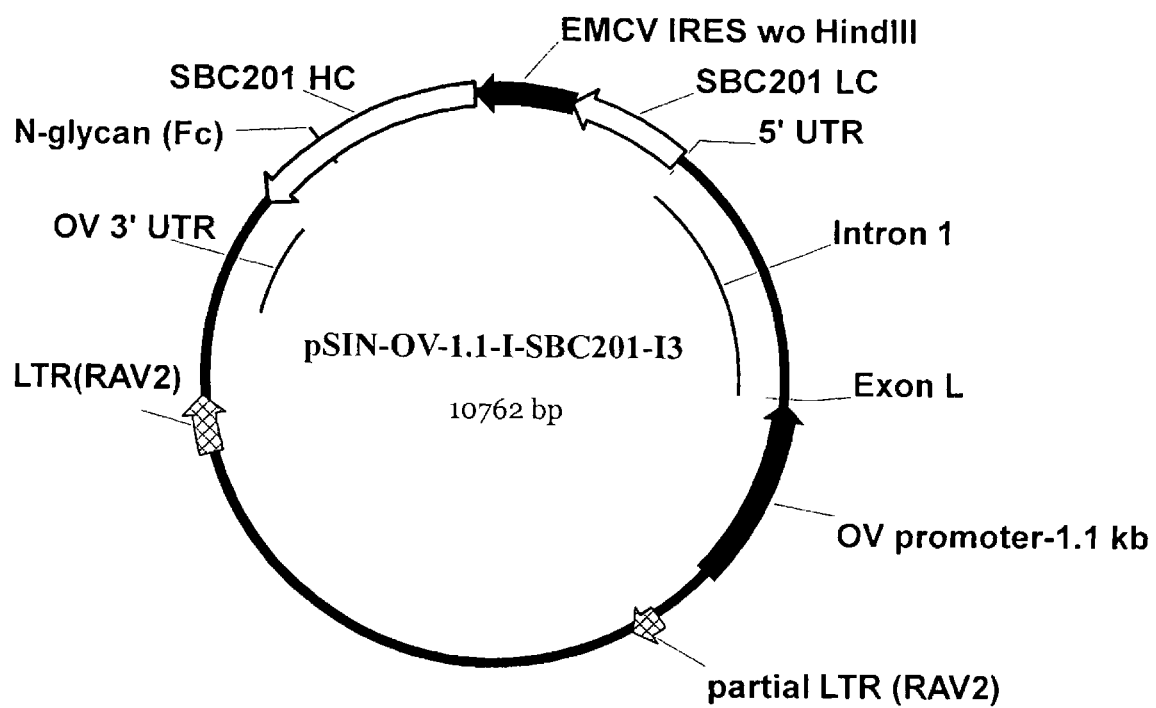
FIG. 9 shows a map of vector pSIN-OV-1.1-I-SBC201-I3. The sequence of the vector is shown in SEQ ID NO: 6. Some of the features of pSIN-OV-1.1-I-SBC201-I3 are specified by the following nucleotide sequences: CDS-9206.10618; promoter-2835.3966; 5'UTR-1182.1198; exon-2788.2834; LTR-7610.7955; LTR-4335.4507; intron-1199.2787; 5'UTR-1182.1198; CDS-474.1181; 3'UTR-8518.9191; and glycosil site-9659.9661.

A 8517 by KpnI/KpnI fragment of pSIN-OV-1.1-I-SBC201 was ligated to a 1919 bp KpnI/SexAI fragment of pSIN-OV-1.1-I-SBC201 and 326 by KpnI/SexAI fragment of syn IRES3 090508 (SEQ ID NO: 9) to produce pSIN-OV-1.1-I-SBC201-13 shown in FIG. 9 and in SEQ ID NO: 6. Alternative cloning strategies are available to produce pSIN-OV-1.1-I-SBC201-13, as is understood by a practitioner of skill in the art.

EXAMPLE 2

Production Of Transgenic Chickens Using pSIN-OV-1.1-I-SBC201-I3

Retroviral particles pseudotyped with the VSV envelope protein and containing pSIN-OV-1.1-I-SBC201-I3 were produced as described in US patent publication No. 2007/0077650, published Apr. 5, 2007, the disclosure of which is incorporated in its entirety herein by reference. Virus was harvested at 48 hours post-transfection, concentrated and on the same day approximately 7 microliters injected into the subgerminal cavity of stage X eggs. Eggs were resealed and incubated until hatch. The transgenesis level in these hens is estimated at 5% or less.

G1 hens were obtained by crossing G0 transgenic roosters to wild type hens and screening for transgenic offspring. Egg white from G1 hens produced substantially more antibody than produced in the chimeric G0 hens, as expected. The amino acid sequence of the anti-CD20 antibody produced is shown in FIG. 2.

EXAMPLE 3

Carbohydrate Analysis of Transgenic Poultry Derived Anti-CD20

Anti-CD20 was prepared from egg white obtained from eggs laid by G1 transgenic chickens produced as described in Example 2 using a Protein A column, as is understood in the art.

MALDI-TOF-MS (Matrix assisted laser desorption ionization time-of-flight mass spectrometry) analysis and ESI MS/MS (electrospray ionization tandem mass spectrometry) were performed on the oligosaccharides after release from the peptide backbone of the purified avian derived anti-CD20. Permethylated N-glycan structures identified by MALDI-TOF-MS are shown in FIG. 2. Approximate m/z are indicated for each of the structures.

The permethlyated N-glycans were also analyzed by nanospray ionization (NSI), as is understood in the art. The NSI method of analysis revealed additional oligosaccharide structures not detected using MALDI-TOF-MS, some of which have a fucose residue. For example, the fucose residue may be attached through an N-acetylglucosamine of the reducing terminus. It has been estimated that approximately 1% to 3% of the oligosaccharides attached to the antibodies have an attached fucose. Approximate m/z are indicated in FIGS. 1 and 2 for each of the structures.

EXAMPLE 4

Anti-CD20 CDC (Complement Dependent Cytotoxicity) Determination

Figure 6:
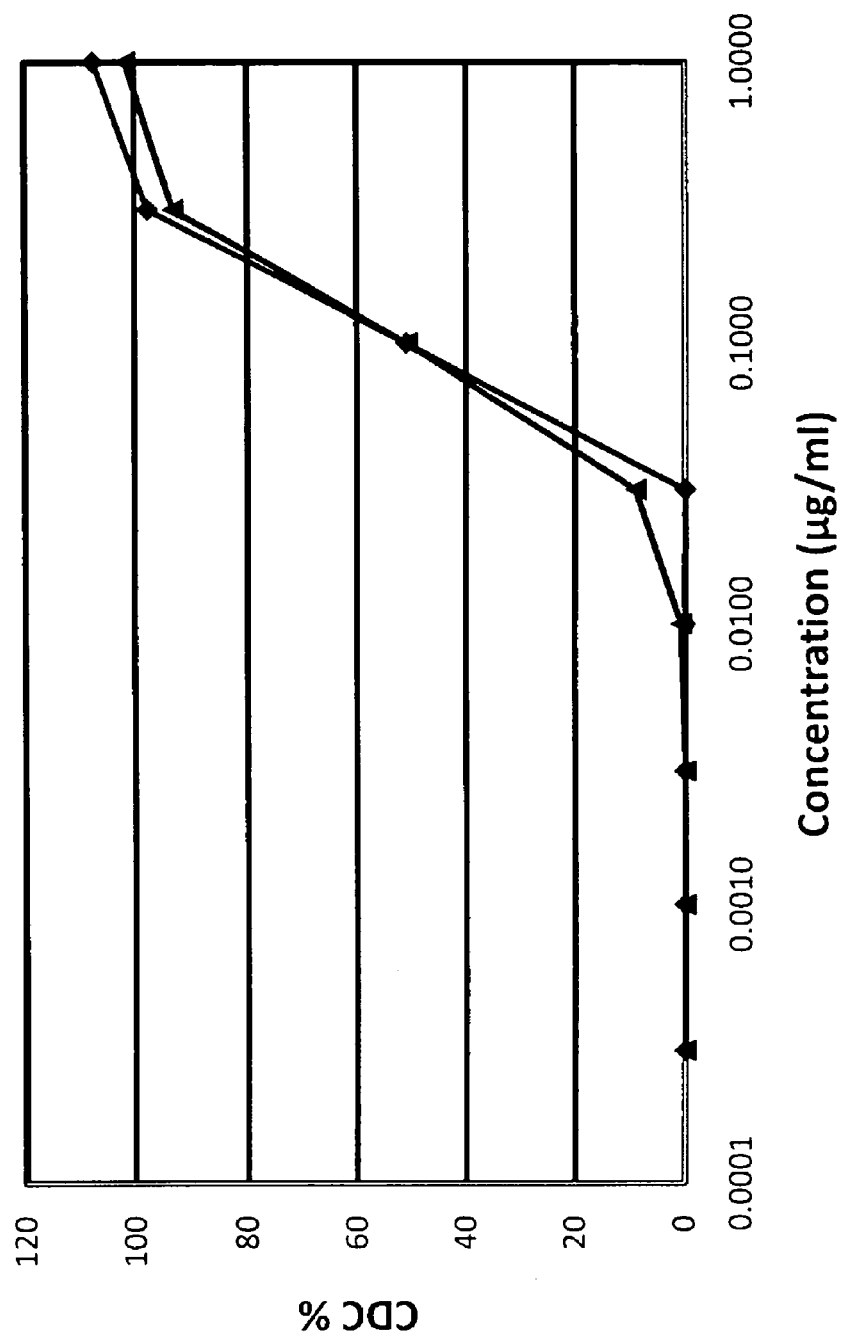
FIG. 6 shows the CDC activity of the anti-CD20 produced in accordance with the invention as described in Examples 1 to 3 (filled triangle) compared to the same anti-CD20 antibody produced in CHO cells (filled diamond).

Daudi cells were washed and resuspended in a serum free medium to a concentration of about $5 \times 10^4$ cells per ml and 50 µl aliquots of the cells were added to the wells of a 96 well microtiter plate. 50 µl aliquots of anti-CD20 antibody produced as described in Examples 1 and 2 above were prepared having concentrations shown in FIG. 6 (concentration ranges from 0.3 ng/ml to 1000 ng/ml). The antibody aliquots were added to wells of the 96 well microtiter plate containing the Daudi cells. 50 μl of 1:3 diluted normal human serum complement solution was added to each sample well, the solution was gently mixed then incubated at 37° C. After 2 hours of incubation, 30 μl of CellTiter-Blue Reagent® was gently mixed into each well followed by 16 hours of incubation at 37° C. The optical density was determined using a fluorometer at $560_{EX}/590_{EM}$ nm and percentage of cellular lysis was calculated. The assay was repeated using commercially available anti-CD20 made in CHO cells having the same heavy chain and light chain amino acid sequences as the avian derived anti-CD20. Results are shown in FIG. 6.

EXAMPLE 5

Anti-CD20 ADCC (Antibody Dependent Cellular Cytotoxicity) Determination

PBMCs (Peripheral blood mononuclear cells) to be used as human effecter cells were prepared from blood of a healthy donor by separation in Ficoll-Hypaque density gradient. After separation, the cells were washed three times in 1×PBS.

Figure 7:
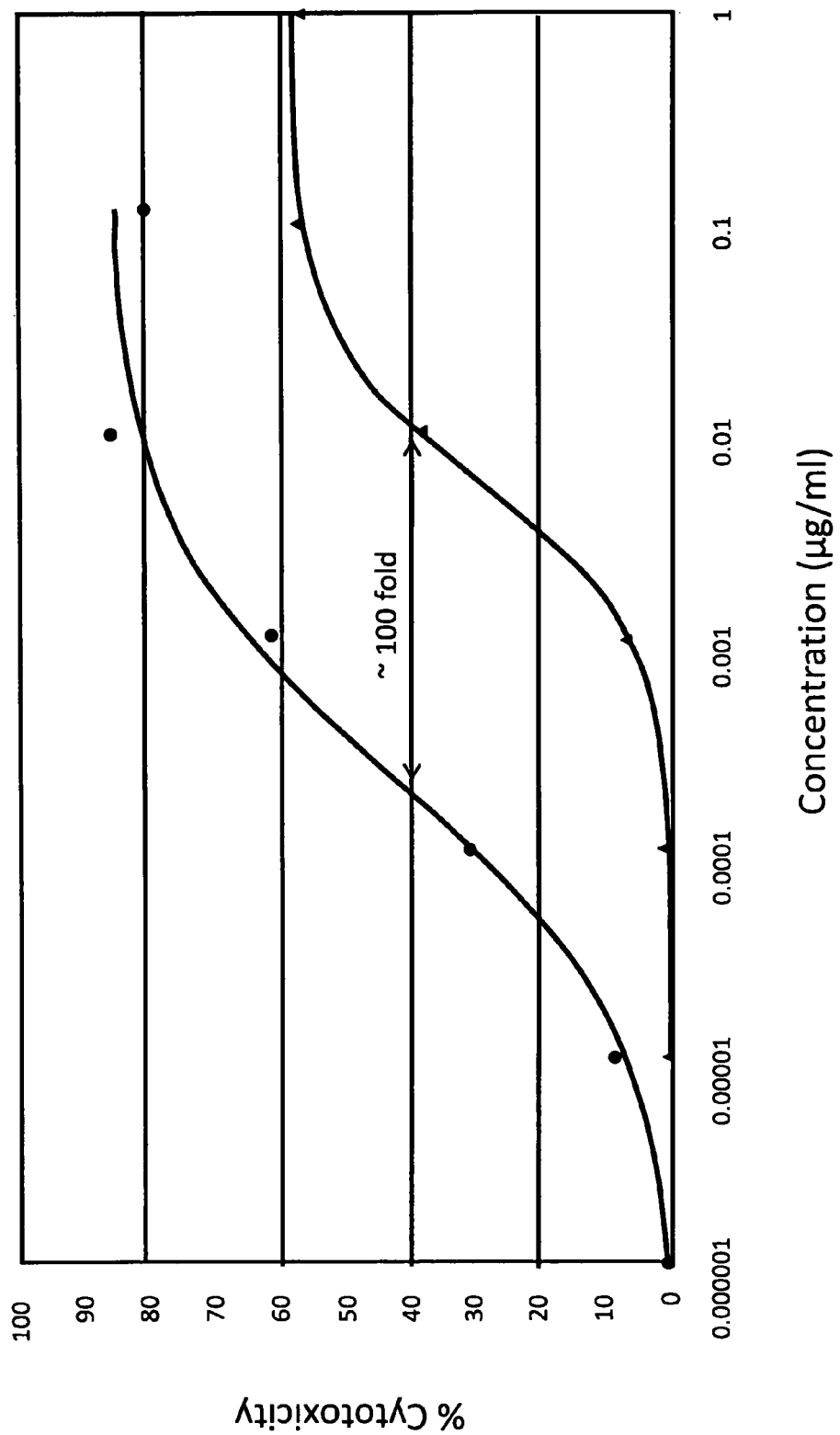
FIG. 7 shows the ADCC activity of the anti-CD20 produced in accordance with the invention as described in Examples 1 to 3 (filled circle) compared to the same anti-CD20 antibody produced in CHO cells (filled triangle).

Daudi cells were harvested, washed, and resuspended in RPMI-1640 plus 10% HIA FBS, 1× pen/strep, 1×L-glutamin to a concentration of 1×10⁶ cells per ml. Calcein-AM (Calcein acetoxymethyl ester) was added to the Daudi cells to a final concentration of 15 μM and the mixture was incubated at 37° C. for 30 min. The cells were then washed twice with 1×PBS and were resuspended in RPMI-1640 plus 10% HIA FBS, 1× pen/strep, 1×L-glutamin. Equal volumes of labeled target and PBMC suspensions were mixed, resulting in a ratio of PBMC Effector:Daudi Target Cells of about 50:1. 100 μl of the cell mixture was added to each well of a 96-well plate. 50 μl aliquots of antibody (concentrations ranging from 0.01 ng/ml to 10,000 ng/ml) produced as described in Examples 1 and 2 were added to the wells. The samples were incubated for 4 h at 37° C. in a 5% $CO_2$ incubator and then centrifuged at 300×g for 3 min. 75 μl of supernatant were removed from each well and percentage of cytolysis was determined by analyzing optical density. The assay was repeated using commercially available anti-CD20 made in CHO cells having the same heavy chain and light chain amino acid sequences as the avian derived anti-CD20. Results are shown in FIG. 7. It can be seen the anti-CD20 antibody produced in accordance with the invention has a surprisingly high ADCC.

EXAMPLE 6

Anti-CD20 PK Determination

Figure 8:
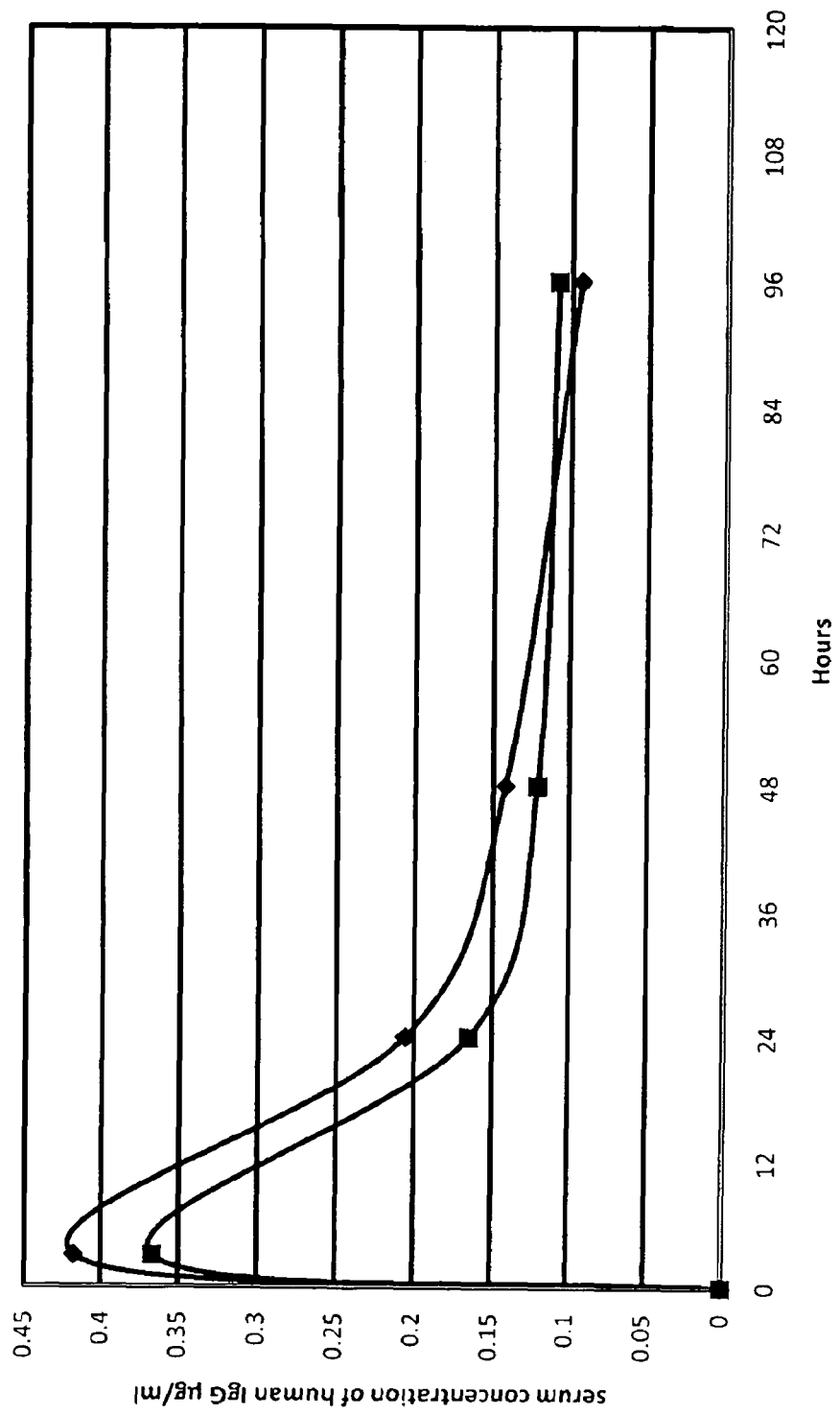
FIG. 8 shows the PK of the anti-CD20 produced in accordance with the invention as described in Examples 1 to 3 (filled diamond) compared to the same anti-CD20 antibody produced in CHO cells (filled square).

A healthy rat was injected with 0.1 mg of anti-CD20 produced as described in Examples 1 and 2 above per kilogram of body weight. A control rat was injected with commercially available anti-CD20 made in CHO cells having the same heavy chain and light chain amino acid sequences as the avian derived anti-CD20. The antibody was assayed for by Elisa to determine serum concentration at time points over a four day period. The results are shown in FIG. 8.

All documents (e.g., U.S. patents, U.S. patent applications, publications) cited in the above specification are incorporated herein by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

---

What is claimed is:

1. A composition comprising an isolated mixture of cytotoxic anti-CD20 antibody molecules produced in a transgenic avian, wherein the antibody molecules comprise a heavy chain and a light chain whose amino acid sequences set forth in SEQ ID NOs: 4 and 5, wherein the isolated mixture of cytotoxic anti-CD20 antibody molecules exhibit an increased level of cytotoxicity as compared to anti-CD20 antibody molecules produced in CHO cells and having the same amino acid sequence.

2. The composition of claim 1, wherein the isolated mixture of the anti-CD20 antibody molecules are produced in tubular gland cells of the transgenic avian.

3. The composition of claim 2, wherein the transgenic avian is selected from the group consisting of a chicken, a quail and a turkey.

4. The composition of claim 3, wherein the transgenic avian is a chicken.

5. The composition of claim 4, wherein the cytotoxic anti-CD20 antibody molecules are isolated from egg white of the transgenic chicken.

6. The composition of claim 5, wherein about 95% or more of the N-linked oligosaccharide structures present on the antibody molecules do not contain fucose.

* * * * *